United States Patent
Baratier et al.

(10) Patent No.: US 10,660,564 B2
(45) Date of Patent: May 26, 2020

(54) APPARATUS, SYSTEM AND METHOD FOR DETERMINING COMPLIANT USE OF AN INTRAORAL APPLIANCE

(75) Inventors: Ludovic Baratier, Cailloux-sur-Fontaines (FR); Fabrice Paublant, Saint Cye au Mont d'Or (FR); Denis Ropp, Ugines (FR); Yannick Favre, Epagny (FR); Ronald James Huby, New South Wales (AU); Muditha Pradeep Dantanarayana, New South Wales (AU)

(73) Assignee: RESMED SAS, Saint Priest (FR)

( * ) Notice: Subject to any disclaimer, the term of this patent is extended or adjusted under 35 U.S.C. 154(b) by 838 days.

(21) Appl. No.: 13/700,650

(22) PCT Filed: May 27, 2011

(86) PCT No.: PCT/EP2011/058778
§ 371 (c)(1),
(2), (4) Date: Feb. 19, 2013

(87) PCT Pub. No.: WO2011/147985
PCT Pub. Date: Dec. 1, 2011

(65) Prior Publication Data
US 2013/0140289 A1 Jun. 6, 2013

Related U.S. Application Data

(60) Provisional application No. 61/349,266, filed on May 28, 2010.

(30) Foreign Application Priority Data

May 28, 2010 (FR) ..................................... 10 54138
May 28, 2010 (FR) ..................................... 10 54139
(Continued)

(51) Int. Cl.
*A61B 5/00* (2006.01)
*B23K 26/352* (2014.01)
(Continued)

(52) U.S. Cl.
CPC .............. *A61B 5/4833* (2013.01); *A61C 7/36* (2013.01); *A61C 19/04* (2013.01); *A61C 19/045* (2013.01);
(Continued)

(58) Field of Classification Search
CPC .............................. A61B 5/4833; A61C 19/04
See application file for complete search history.

(56) References Cited

U.S. PATENT DOCUMENTS 4,708,491 A * 11/1987 Luitje .................. G04G 99/006
368/156
6,731,213 B1 5/2004 Smith
(Continued)

FOREIGN PATENT DOCUMENTS

WO   WO 2007/143624      12/2007
WO   WO 2008/039921       4/2008
WO   WO 2008039921 A2 *   4/2008   ............. A61F 5/566

OTHER PUBLICATIONS

International Search Report for PCT/EP2011/058778 dated Sep. 6, 2011.
(Continued)

*Primary Examiner* — Daniel L Cerioni
*Assistant Examiner* — Yasmeen S Warsi
(74) *Attorney, Agent, or Firm* — Nixon & Vanderhye, P.C.

(57) ABSTRACT

A compliance monitoring system (40) for an intraoral appliance comprises a power source (460), a detector (410) for detecting when the intraoral appliance is positioned in the mouth for use, a recorder (430) configured to record mea-
(Continued)

surement data, and a transponder (440) configured to communicate the measurement data. The monitoring system is adjustable based on a particular property of a patient or a group of patients.

37 Claims, 8 Drawing Sheets

(30) Foreign Application Priority Data

| May 28, 2010 | (FR) | .................................... 10 54140 |
| May 28, 2010 | (FR) | .................................... 10 54142 |
| May 28, 2010 | (FR) | .................................... 10 54143 |

(51) Int. Cl.
  *A61C 7/36* (2006.01)
  *A61F 5/56* (2006.01)
  *A61C 19/045* (2006.01)
  *A61C 19/04* (2006.01)
  *B33Y 80/00* (2015.01)
  *A61F 2/48* (2006.01)
  *A61B 18/00* (2006.01)
  *G07C 3/04* (2006.01)
  *A61B 90/00* (2016.01)

(52) U.S. Cl.
  CPC ............ *A61F 5/566* (2013.01); *B23K 26/352* (2015.10); *A61B 2018/00988* (2013.01); *A61B 2090/0803* (2016.02); *A61F 2002/488* (2013.01); *B33Y 80/00* (2014.12); *G07C 3/04* (2013.01)

(56) References Cited

U.S. PATENT DOCUMENTS

| 7,146,982 B2 | 12/2006 | Mousselon et al. |
| 2004/0029068 A1 | 2/2004 | Sachdeva et al. |
| 2005/0100866 A1* | 5/2005 | Arnone ................ A61B 5/0088 433/215 |
| 2006/0166157 A1 | 7/2006 | Rahman et al. |
| 2006/0240374 A1 | 10/2006 | Wen |
| 2007/0134615 A1* | 6/2007 | Lovely ................ A61B 5/0088 433/29 |
| 2007/0277836 A1 | 12/2007 | Longley |
| 2007/0283973 A1 | 12/2007 | Longley |
| 2008/0227046 A1 | 9/2008 | Lowe et al. |
| 2009/0105523 A1 | 4/2009 | Kassayan et al. |
| 2010/0087896 A1 | 4/2010 | McCreery |

OTHER PUBLICATIONS

Written Opinion of the International Searching Authority dated Sep. 6, 2011.
Extended European Search Report dated May 23, 2018, issued in European Patent Application No. 17164461.0.

* cited by examiner

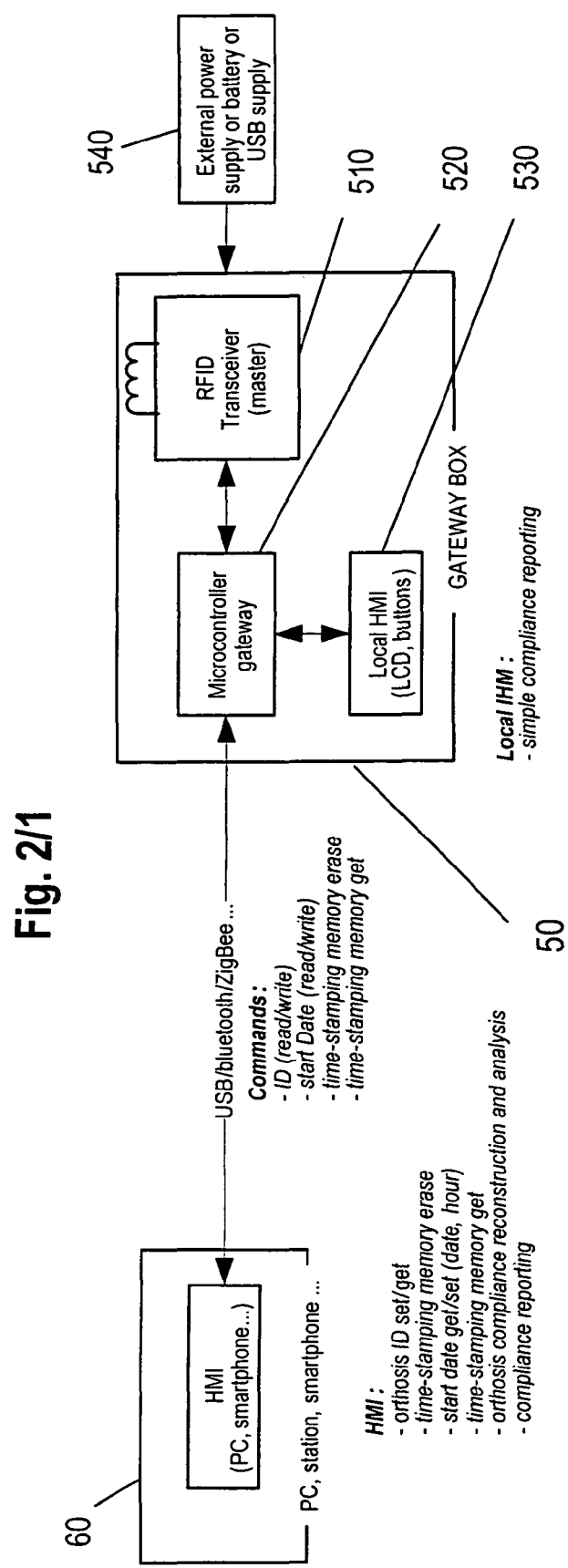
Fig. 2/1

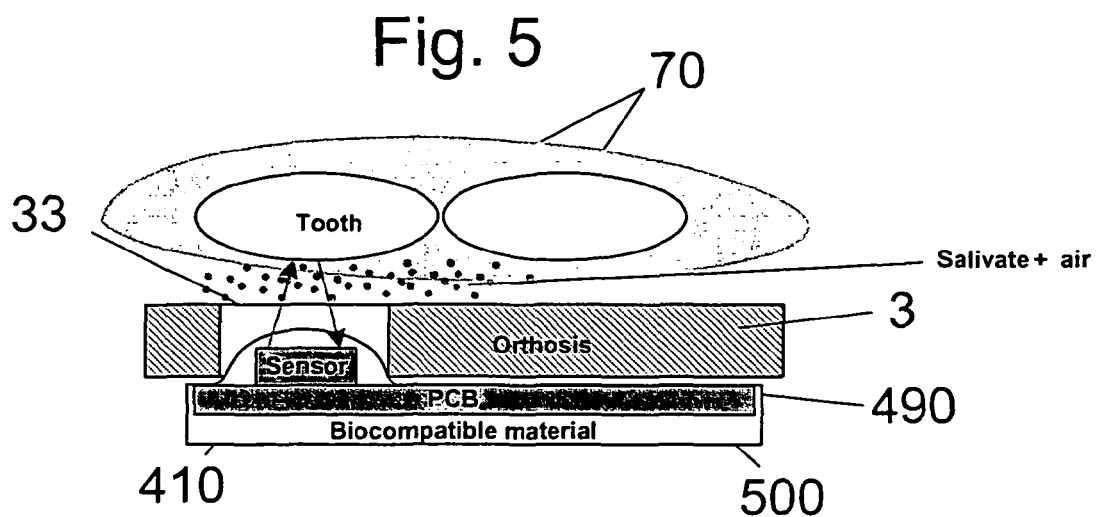
Fig. 5
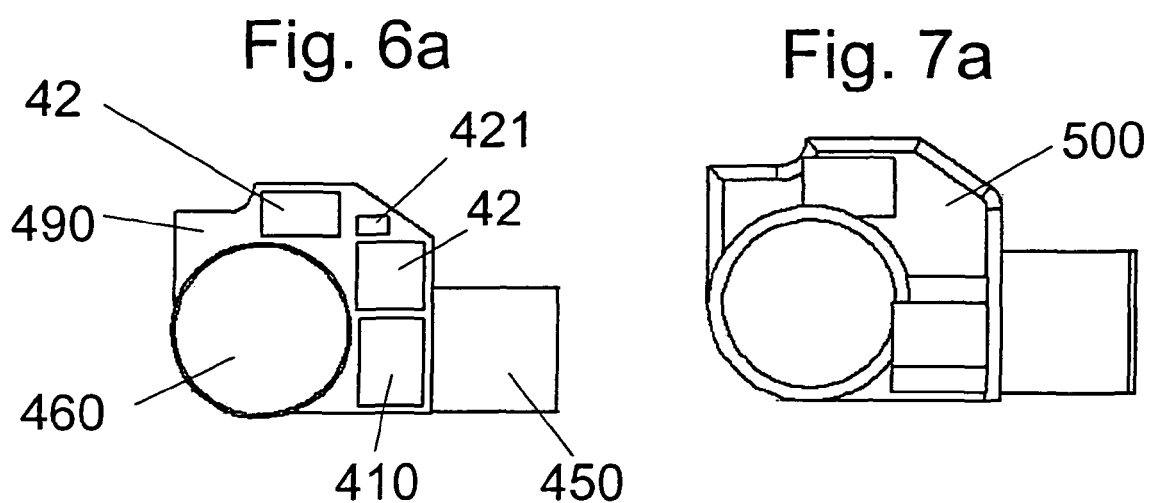
Fig. 6a
Fig. 7a
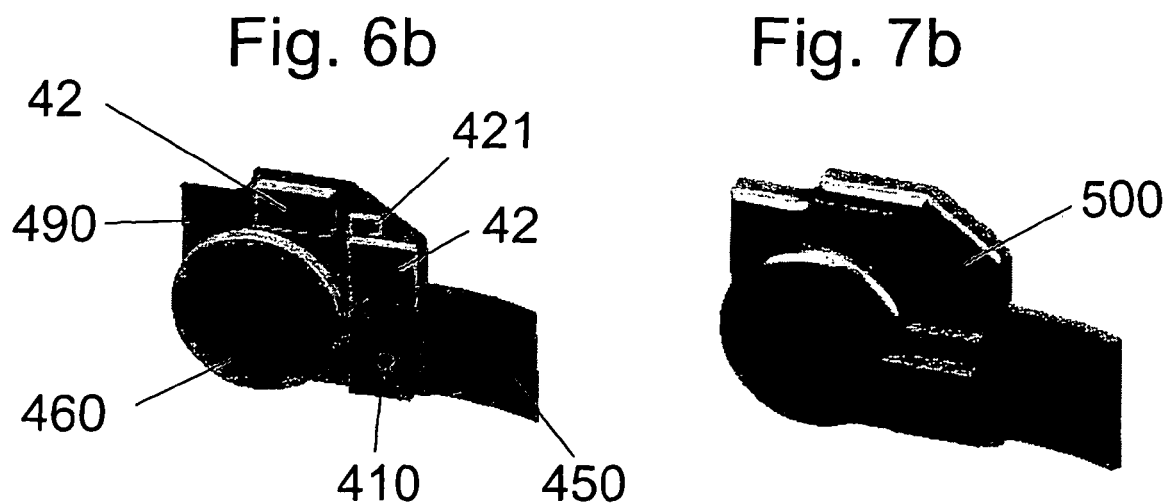
Fig. 6b
Fig. 7b

APPARATUS, SYSTEM AND METHOD FOR DETERMINING COMPLIANT USE OF AN INTRAORAL APPLIANCE

This application is the U.S. national phase of International Application No. PCT/EP2011/058778 filed 27 May 2011 which designated the U.S. and claims priority to U.S. Provisional Application No. 61/349,266 filed 28 May 2010, FR1054143 filed 28 May 2010, FR 1054142 filed 28 May 2010, FR 1054139 filed 28 May 2010, FR 1054140 filed 28 May 2010, and FR 1054138 filed 28 May 2010, the entire contents of each of which are hereby incorporated by reference.

The present invention relates to the field of intraoral appliances, such as mandibular repositioning devices, bruxism treatment devices, etc. More generally the invention relates to oral appliances, for instance in the field of treatments of sleep disorders. More precisely it, inter alia, relates to the use of monitoring compliance of treatment by patients, for instance, by patients suffering from sleep disordered breathing such as obstructive sleep apnoea syndrome and snoring, and to an apparatus and a method for determining compliant use of an intraoral appliance.

Medical compliance is a significant issue in the care and treatment of many chronic disorders. This is particularly true for Sleep Disordered Breathing and in particular Obstructive Sleep Apnoea Syndrome (OSAS), where associated risks factors include excessive daytime somnolence leading to road and work-related accidents as well as increased cardiovascular risks. Indeed failure to respect sufficient compliance rate with treatment for Obstructive Sleep Apnoea Syndrome makes the treatment inadequate and warrants a change of prescription to an alternative treatment by the medical professional who follows the patient. In countries such as the United States, Australia, Canada and France, professions which are particularly at risk for traffic accidents such as truck and bus drivers, if diagnosed with the pathology, need to show objective evidence of efficiency of treatment and sustained compliance to be able to resume their professional activity. Positive Airway Pressure (PAP) is the gold standard for treatment of OSAS and these are all equipped with compliance monitors that can be easily downloaded by the healthcare professional to assess patient compliance to treatment. Mandibular Repositioning Device (MRD) is a validated treatment of OSAS for patients who do not tolerate or are not compliant to PAP. One of their limitations however is the impossibility so far to rely on objective data to assess the number of hours during which the device is worn every night by the patient.

Some apparatuses and method for measuring and determining compliant use of orthodontic devices have been developed. For instance, the patent application US 2006/0166157 published on Jul. 27, 2006 describes a method and apparatus to monitor compliance in orthodontic devices such as an orthodontic brace, a retainer, a mouth guard, a bruxism treatment device, or a nightguard. However, the orthodontic devices of US 2006/0166157 are intended to be used for a maximum of several months, and the solutions proposed to monitor compliance of these devices are not adapted for orthodontic devices having a service-life of several years. In particular, the known solutions do not satisfy the requirements imposed by such long service-life, in particular with regard to energy consumption, material degradability, etc. Moreover, the known compliance monitor may be easily tricked by a patient or be subject to inaccurate and faulty monitoring. Thus, the known devices are not suited to provide an objective evidence of efficiency of treatment.

Intraoral appliances are generally produced using dental impressions. This is time consuming and involves intensive labour work. Depending on the skills of the dentist, dental impressions are often not accurate enough to allow production of a correct dental cast and thus of a perfectly fitting intraoral appliance. In some cases, the intraoral appliance or dental casts then needs to be corrected or re-manufactured. The conventional production using dental impressions require physical shipment of the impressions, which is time consuming. Moreover, a considerable number of dental impressions also gets damaged during the transportation. Known customized intraoral appliance manufactured by using dental impressions made of acrylic resin. Such appliances tend to be relatively bulky and heavy which reduces the wearing comfort for the patient.

It is an object of the present invention to provide an alternative or improved solution. Preferably the present invention overcomes or ameliorates the disadvantages of the prior art.

An aspect of the present technology is a method and apparatus for monitoring compliance of a patient receiving dental device therapy. There are proposed an apparatus, system and method for determining compliant use of an intraoral appliance, such as a mandibular repositioning device, a bruxism treatment device, or the like as well as such device comprising a compliance monitor and its uses. The proposed device, use, apparatus, system and method are particularly adapted for determining compliant use of a mandibular repositioning device specifically designed for OSAS.

Another aspect of the present technology is a method for locating sensors and electronic components in an intraoral appliance in a way that will be comfortable for a patient.

Another aspect of the present technology is a device, use, apparatus, system and method for determining compliant use of an intraoral appliance which has a low energy consumption so that it can operate during several years in a normal clinical setting without being replaced.

Another aspect of the present technology is a device, use, apparatus, system and method for determining compliant use of an intraoral appliance which may be easily replaced without destruction of the appliance.

Another aspect of the present technology is a device, use, apparatus, system and method for determining compliant use of an intraoral appliance which is very compact and does not reduce the comfort of the patient using the appliance.

Another aspect of the present technology is a device, use, apparatus, system and method for determining compliant use of an intraoral appliance with an option to use it in clinical trials where precise data is required or in clinical practice with processed data to preserve patient privacy.

Another aspect of the present technology is to offer a detection method that is reliable and that can not be tricked by the patient intentionally or unintentionally.

A compliance monitoring system for an intraoral appliance is provided which may comprise a power source, a detector, and a transponder. The detector is adapted to and may be used for detecting when the intraoral appliance is positioned in the mouth of a patient for use. Preferably, the detector measures data. Moreover, the transponder is configured to communicate the measurement data and the monitoring system may be adjustable, for instance, based on a particular property such as a unique characteristic of a patient or a group of patients or of within a mouth.

Preferably, the particular property of a patient or a group of patients is a physical property including one or more of the group consisting of colour, teeth enamel, temperature, distance, angle, and/or shape. The physical property, particularly the colour, may relate any portion of the oral cavity such as the gum, the teeth or tissues inside the cheek.

Preferably, the monitoring system, preferably the detector, comprises at least one signal emitter and at least one signal receiver. The at least one signal emitter and the at least one signal receiver may be any kind of signal emitter and signal receiver which are adapted to measure a particular property of a patient or a group of patients in an adjustable monitoring system. Preferably, the signal emitter and/or the signal receiver may be configured as light emitter and light receiver, respectively. More preferably, the signal emitter is an infrared-light emitter and the light receiver is an infrared-light receiver. The compliance monitoring system may furthermore comprise a signal emitter and signal receiver configured as a sound emitter and a sound receiver. More preferably, the signal emitter is an ultrasound emitter and the signal receiver is an ultrasound receiver. Moreover, the signal emitter may be a current emitter, preferably a respectively driven electrode, and the signal receiver a voltage receiver, preferably a respectively driven electrode.

The at least one signal emitter and/or the at least one signal receiver may be adjustable and/or may be adapted for being calibrated. Moreover, the monitoring system may be adjustable, preferably in an automated manner, by adjusting one or more physical parameters, preferably of the system and more preferably of the detector.

The monitoring system may be adjustable by adjusting one or more physical parameters of the signal receiver and/or signal emitter such as wave length, intensity, amplitude, frequency, phase, modulation, coding and/or impedance. Preferably, the signal emitter and signal receiver are separately adjustable.

The signal emitter and the signal receiver may be configured to be operated with a wavelength adapted for reflection on a patient's tooth. Preferably, the emitter and the receiver are configured to be operated with a wavelength adapted for a reflection on the specific enamel of a patient's tooth or teeth, for the individual relative position between emitter, receiver and tooth, and/or considering parameters such as distance, angle, shape/geometry, colour, surface properties, and/or temperature.

The detector may be configured as a reflective detector which preferably comprises the at least one signal emitter and/or the at least one signal receiver.

The transponder may be any kind of communication system configured to communicate the measurement data. Preferably the transponder is an induction signal system or a radiofrequency identification transponder having a radiofrequency identification modulator/demodulator and preferably a data storage medium.

The compliance monitoring system may further comprise a recorder, which is preferably configured to record measurement data. The compliance monitoring system may also comprise a means for periodical activation of the signal emitter and/or signal receiver, preferably a reflective infrared-detector, and of the recorder. The periodical activation means of the compliance monitoring system preferably comprises a crystal, an oscillator, a prescalor and/or a timer.

The compliance monitoring system may comprise a processor to process the measurement data and associated time data. Moreover, the compliance monitoring system may be configured to record said processed measurement data and associated processed time data. The processed measurement data and/or associated processed time data may correspond to the accumulated period of time which the intraoral appliance has been used, for instance, in a specific day. Most preferably, the processor may be programmable to either store raw measurement data and associated time data, for instance for use in clinical trials or researches, or to store processed measurement data and associated time data, for instance for use in clinical practice.

Moreover, an intraoral appliance, preferably a mandibular repositioning device, is proposed which comprises a compliance monitoring system. Moreover, the intraoral appliance may comprise at least one splint. The at least one splint may be further designed for receiving the compliance monitoring system, preferably in a position where the detector faces at least one portion of the oral cavity of a patient, most preferably at least one of the teeth.

Moreover, an apparatus/system for determining compliant use of an intraoral appliance is proposed which comprises the compliance monitoring system and a processing system. The processing system may comprise a communication device and an analyzing device. The communication device may be configured for receiving data, for instance, measurement and/or time data, from and for sending command data to the compliance monitoring system. The analyzing device may be communicatively coupled to the communication device. Moreover, the analyzing device may be configured for identifying, collecting, and for organizing information from the monitoring system, preferably via the communication device, in order to determine and/or report compliant or non-compliant use of the intraoral appliance.

Another aspect relates to a method for determining compliant use of the intraoral appliance with the compliance monitoring system with the steps of measuring at least one value $V_{CE}$ indicative of a signal received by a signal receiver and, preferably, determine whether a tooth is detected or not by comparing the value $V_{CE}$ to a threshold value.

Generally, the measured data may be a directly or indirectly measured value which is indicative of a compliant use. The measured data may be at least one of:
   current, voltage, and/or resistance; and/or
   wave length, intensity, amplitude, frequency, phase, modulation, coding and/or impedance of a signal, particularly of sound or light such as infrared light; and/or
   individual relative position between the monitoring system and tooth or teeth, gum, and/or inside of the cheek, such as distance and/or angle; and/or
   individual geometry such as shape, temperature, colour, surface properties and/or reflection characteristics of the tooth or teeth, gum and/or inside of the cheek, particularly of the specific enamel of a patient's tooth or teeth; and/or
   type of tooth or teeth, and/or
   characteristic of a fluid media such as saliva and/or ambient air.

The method may furthermore comprise the step of measuring a first value $V_{CE1}$ indicative for the ambient and/or artificial light received by the signal receiver. In other words the first value $V_{CE1}$ is indicative for the signal received while the signal emitter does not emit a signal. Preferably a second value $V_{CE2}$ is measured when the signal emitter does emit a signal. The second value $V_{CE2}$ is thus indicative for the total signal received by the signal receiver while the signal emitter emits a signal. The method moreover may comprise a calculation of the difference delta $V_{CE}$ between the second value $V_{CE2}$ and the first value $V_{CE1}$, preferably for filtering ambient noise from the received signal.

Preferably, the value $V_{CE}$ to be compared with the threshold value may be the difference delta $V_{CE}$. The signal received by the signal receiver is preferably based on the signal emitted by the signal emitter. The signal may be influenced by a physical property, preferably by a unique characteristic, of the patient.

The compliance monitoring system may be adjusted and/or calibrated. Preferably, at least one measurement is therefore conducted outside the patient's oral cavity and a plurality of measurements are conducted inside the patient's oral cavity. Preferably, the settings of the compliance monitoring system, the settings of the signal emitter, and/or signal receiver are changed or varied. The signal emitter and/or signal receiver is adjusted, preferably by changing the hardware settings of the compliance monitoring system, of the signal emitter, and/or of the signal receiver, more preferably by changing a wiring configuration of the compliance monitoring system, most preferably by using or switching different electrical components such as resistors.

The threshold value and/or the preferred adjustments of the signal emitter and/or signal receiver may be determined during the calibration. Preferably, the calibration comprises measuring a plurality of differences data $V_{CE\_x}$ obtained for different adjustments of the signal emitter and signal receiver in at least two different setups. One setup may be with the intraoral appliance in the application position and one setup may be with the intraoral appliance in a position outside the oral cavity.

According to one aspect, a method for producing an intraoral appliance, preferably in accordance with a method for determining a compliant use of the intraoral appliance, may comprise a step of automated laser sintering of the oral appliance, the oral appliance preferably also including means for attaching and positioning the compliance monitoring system.

According to another aspect the method may comprise the steps of obtaining a first three-dimensional data set, preferably of the lower jaw and teeth of a patient, of the upper jaw and teeth of a patient and/or the occlusal plane of closed jaws of a patient. Preferably, the method comprises the step of obtaining or generating a second three-dimensional data set, namely of a customized oral appliance, by means of computer aided design, based on the first three-dimensional data set. The method may also comprise the step of automated manufacturing of customized (intra) oral appliance.

According to another aspect is a compliance monitoring system with an arrangement that enables great compactness of the system. Such arrangement is also very efficient for measuring compliance of the system as it may be adapted to the specific enamel of the patient. In such aspects a reflective infra-red detector may be used in combination with other components to form the compliance monitoring system.

According to another aspect is a compliance monitoring system with an arrangement that enables retrieving any data from its data storage medium(s) at any time, including in case of battery breakdown or failure. Such retrieval of data may further be performed without damaging the system nor the intraoral appliance. In such aspects a radiofrequency identification transponder may be used in combination with the main components forming the compliance monitoring system.

According to a further aspect is a compliance monitoring system with an arrangement that enables operation of the system with very low power consumption, which is thus very advantageous for increasing the service-life of the system. Further the proposed arrangement enables using electronic components available on the shelve, much less expensive than specifically designed components. In such an aspect a buffer may be used with the cooperation of the data storage mediums provided in the system.

According to a further aspect is a compliance monitoring system with an arrangement that enables the system to be easily and removably fitted in most types of intraoral appliances. Further, the system does not cause discomfort to the user of the oral appliance. Such an aspect comprises the encapsulation of the components of the system in a single-piece element with biocompatible material.

According to still another aspect is a method for producing a mandibular repositioning device to be coupled with a removable compliance monitoring system. The proposed method is cost effective, and very easy to perform. It may further be entirely automated.

The device, use, apparatus, system and method may also at least partially, alternatively or additionally, be defined by the below discussed aspects. One or more features of each aspects discussed may be combined with one or more features of the same aspects. Additionally and/or alternatively, said one or more features of the aspects may be combined with one or more features of at least one other aspect.

1. A compliance monitoring system for an intraoral appliance, such as a mandibular repositioning device, comprising:
 a power source;
 a switch detector for detecting when the intraoral appliance is positioned in the mouth for use;
 a recorder powered by the power source, coupled to the switch detector and configured to record measurement data responsive to the switch detector and associated time data; and
 a transponder connected to the recorder and configured to communicate the measurement data and associated time data responsive to a command.

2. The compliance monitoring system of aspect 1, wherein the switch detector is a reflective infra-red detector.

3. The compliance monitoring system of aspect 2, wherein the reflective infra-red detector is configured to be operated with an infra-red wavelength adapted for reflection on the specific enamel of a patient to use the intraoral appliance.

4. The compliance monitoring system of any of aspects 1 to 3, wherein the transponder is a radiofrequency identification transponder, preferably having a radiofrequency identification modulator/demodulator and a data storage medium.

5. The compliance monitoring system of aspect 4, wherein the radiofrequency identification transponder is further connected to the recorder and configured to supply power to said recorder, so that communication of the measurement data and associated time data from the recorder to the radiofrequency identification transponder is possible even in case of breakdown or failure of the power source.

6. The compliance monitoring system of any of aspects 1-5, wherein the recorder further comprises a first data storage medium and/or the transponder further comprises a second data storage medium and wherein the recorder is configured to sequentially send parts of the measurement data and associated time data from the first data storage medium to the second data storage medium of the transponder, so that the second data storage medium operates as a buffer in the communication of the measurement data and associated time data responsive to the command.

7. The compliance monitoring system of any of aspects 1 to 6, further comprising means for periodical activation of the switch detector and recorder.

8. The compliance monitoring system of aspect 7, wherein the periodical activation means comprises a crystal, an oscillator, a prescaler and a timer.

9. The compliance monitoring system of any of aspects 1 to 8, further comprising a processor to process the measurement data and associated time data, wherein the compliance monitoring system is further configured to record said processed measurement data and associated processed time data.

10. The compliance monitoring system of aspect 9, wherein the processed measurement data and associated processed time data correspond to the accumulated period of time the intraoral appliance has been used in a specific day.

11. The compliance monitoring system of any of aspects 9 or 10, wherein the processor is programmable to either store raw measurement data and associated time data for use in clinical trials or researches, or to store processed measurement data and associated time data for use in clinical practice.

12. The compliance monitoring system of any of aspects 1-11, wherein said power source, switch detector, recorder and transponder are connected onto a printed circuit board and encapsulated by a biocompatible material so as to form a single-piece element adapted to be removably coupled with the intraoral appliance.

13. The compliance monitoring system of aspect 12, wherein the transponder is a radiofrequency identification transponder, the compliance monitoring system further comprising an antenna etched onto the printed circuit board.

14. The compliance monitoring system of any of aspects 12 or 13, wherein the biocompatible material is an epoxy resin compatible with moulding over electronic components.

15. The compliance monitoring system of any of aspects 12 to 14, wherein the switch detector is a reflective infra-red detector and the biocompatible material is at least partially transparent to infra-red.

16. The compliance monitoring system of any of aspects 12 to 15, wherein the single-piece element has a shape for being clipped within a cavity of the intraoral appliance.

17. The compliance monitoring system of any of aspects 12 to 15, wherein the single-piece element comprises clipping portions enabling clipping of the compliance monitoring system onto the intraoral appliance.

18. A mandibular repositioning device for treatment of sleep disorders of a patient, comprising at least one splint designed to line the teeth of an upper or lower jaw of the patient, wherein said at least one splint is further designed for receiving the compliance monitoring system of any of aspects 1 to 17.

19. The mandibular repositioning device of aspect 18, wherein the compliance monitoring system is recieved in a position where the switch detector faces at least one of the teeth.

20. An apparatus for measuring and determining compliant use of an intraoral appliance, such as a mandibular repositioning device, comprising:
the compliance monitoring system of any of aspects 1 to 17, and
a processing system comprising a communication device and an analysing device wherein
the communication device is configured for retrieving measurement and time data from and for sending command data to the compliance monitoring system, and
the analysing device is communicatively coupled to the communication device and is configured for identifying, collecting and organising information from the monitoring system via the communication device in order to determine and report compliant or non-compliant use of the intraoral appliance.

21. A method for producing a mandibular repositioning device, preferably according to any one of aspect 18 or 19, comprising a removable compliance monitoring system, preferably according to any one of aspects 1 to 17, to be positioned in a cavity of the device, wherein the design and manufacture of the device is made with a CADCAM technology with the shape of the device taking into account the three following specifications:
teeth specification depending on the shape of the jaw of the patient;
repositioning specification depending on the specific repositioning of the mandibula that is required to perform for preventing the patient to have sleep disorders; and
encapsulation specification depending on the definite shape of the removable compliance monitoring system.

22. The method of aspect 21, wherein the mandibular repositioning device comprises a first splint and a second splint designed to line the teeth of an upper jaw and the teeth of a lower jaw respectively, and two tie rods for connecting the first and second splints, wherein the tie rods are designed with a length such that the lower jaw is maintained in an advanced position relative to the upper jaw.

23. The method of aspect 22, wherein the mandibular repositioning device is designed such that the tie rods are rotatively mounted on the first and second splints via fixed points of attachment located in the area of the canines and in the area of the second mandibular molar respectively.

24. The method of any of aspects 22 or 23, wherein the mandibular repositioning device is designed such that the tie rods are positioned parallel to the auriculo-orbital plane of the patient or such that the tie rods are positioned relatively parallel to the occlusal plane.

25. The method of any of aspects 22 to 24, wherein the mandibular repositioning device is designed such that the second splint is adapted to shift the point of attachment of the tie rods in the occlusal plane of contact of the lower and upper teeth.

26. The method of aspect 25, wherein the mandibular repositioning device is designed such that the second splint comprises bracket elements protruding from said second splint for shifting the point of attachment of the tie rods, said bracket element being further designed to form a cavity for receiving the removable compliance monitoring system.

27. The method of aspect 26, wherein the mandibular repositioning device is designed such that the bracket elements are distinct elements to be fixed on the second splint.

28. The method of aspect 26, wherein the mandibular repositioning device is designed such that the bracket elements are made as a single part with the second splint, preferably by moulding, fusing or sintering.

29. The method of any of aspects 21-28, wherein the CADCAM process includes, preferably automated, selective laser sintering, preferably layer-wise sintering of a powder material, such as a polymer material, preferably polyamide.

30. The method of any of aspects 21-29, wherein the shape of the device, particularly the opposing surfaces of the first and second splint, is designed so that the opposing surfaces of the first and second splint in an advanced position of the lower jaw are at least partially, preferably completely, abutting against each other, preferably to compensate the Christensen's phenomenon.

BRIEF DESCRIPTION OF THE DRAWINGS

Other features and advantages of the invention will become clear from the following description which is only given for illustrative purposes and is in no way limiting and should be read with reference to the attached drawings on which:

FIG. 5 is a representation of the operation of a reflective infra-red detector positioned in the orthosis within the oral cavity;

FIGS. 6a and 6b are respectively a plane representation and a perspective representation of an embodiment of an electronic circuit forming the proposed monitoring system;

FIGS. 7a and 7b are respectively a plane representation and a perspective representation of the electronic circuit of FIGS. 6a and 6b encapsulated with a biocompatible material;

DETAILED DESCRIPTION OF THE DRAWINGS

General Presentation of a Preferred System

A preferred device, use, apparatus, system and method for determination of compliant use is described below, adapted for being used with an intraoral orthosis for treating sleep disorders, in particular for devices of the mandibular repositioning type.

For an example of such intraoral appliance with which the proposed solution for determination of compliant use could be used, one may refer to patent U.S. Pat. No. 7,146,982 published on Dec. 12, 2006, the content of which is herein fully incorporated by reference.

Figure 1A:
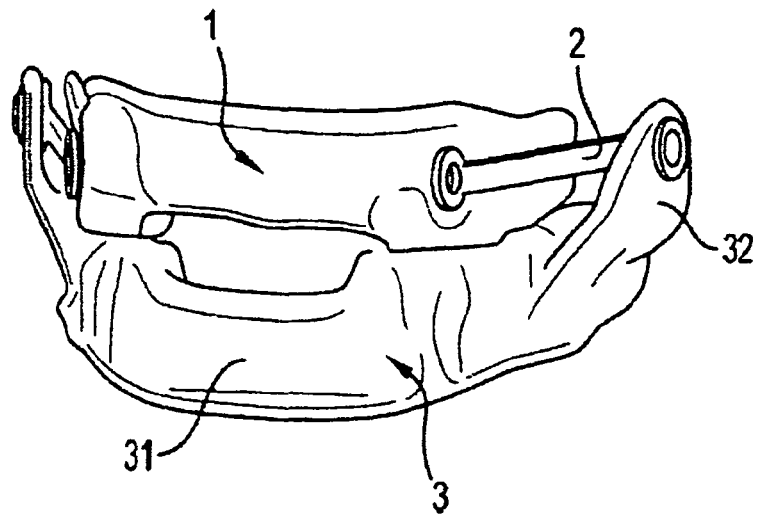
FIGS. 1a and 1b are representations of an intraoral orthosis of the mandibular repositioning type.
Figure 1B:
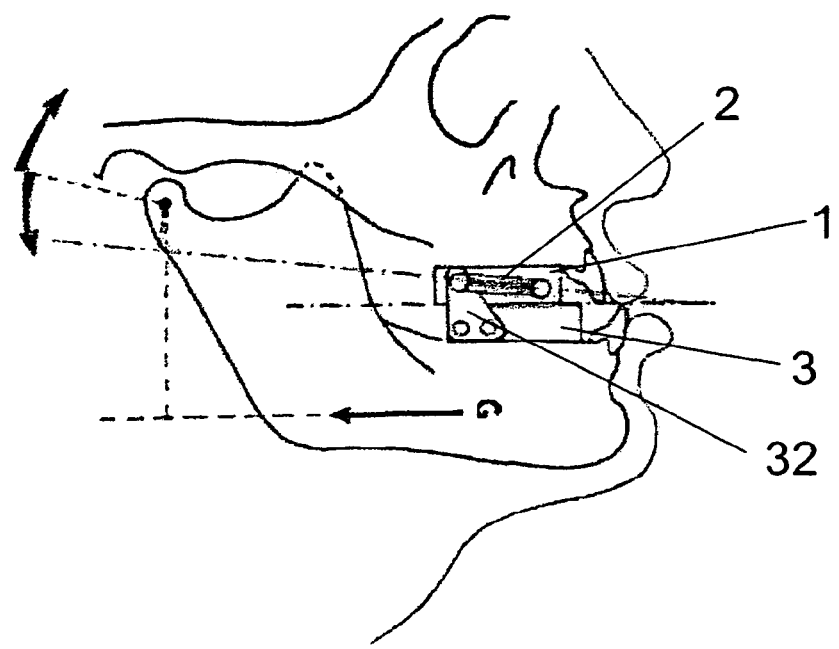

Such device comprises an upper splint (also called upper arch portion) and a lower splint (also called lower arch portion) designed to line the teeth of an upper jaw and the teeth of a lower jaw respectively, wherein two tie rods connect the upper and lower splints, these tie rods being of such a length that the lower jaw is maintained in an advanced position relative to the upper jaw. The tie rods have fixed points of attachment to the splints, for instance on the one hand to the upper splint in the area of the canines, and on the other hand to the lower splint in the area of the second mandibular molar, wherein the tie rods are rotatively mounted on the upper and lower splints. Preferably, the lower splint comprises means for fixation of the tie rods that are adapted to shift the point of attachment of the tie rods in the occlusal plane of contact of the lower and upper teeth. The tie rods which exert traction on the lower splint, and hence on the lower jaw, are positioned parallel to the auriculo-orbital plane also called the Frankfort plane. By virtue of this arrangement, the traction of the tie rods is made along a direction virtually parallel to the occlusal plane, such that the mandibular repositioning device is much less subject to coming loose. The fixation means for shifting the point of attachment of the tie rods may be distinct bracket elements to be fixed on the lower splint, or these fixation means may consist in a bracket element moulded as a single part with the lower splint such as to protrude for shifting the point of attachment of the tie rods. This latter arrangement of a mandibular repositioning device is illustrated in FIG. 1a, the upper splint corresponding to numeral reference 1, the tie rods to numeral reference 2, and the lower splint to numeral reference 3 wherein such lower splint 3 comprises an arch portion 31 and a moulded bracket portion 32 protruding therefrom for shifting the point of attachment of the tie rods 2. FIG. 1b schematically illustrates such mandibular repositioning device in the mouth of a patient, wherein the fixation means for shifting the point of attachment of the tie rods are distinct bracket elements fixed on the lower splint.

The proposed apparatus for determination of compliant use of a mandibular repositioning device first comprises a monitoring system that is to be coupled to the mandibular repositioning device in order to detect whether the device is used by the patient or not.

Such monitoring system is thus adapted to measure and store information regarding the period of time during which the mandibular repositioning device is used, and also to communicate with a remote processing system so that such information may be viewed and possibly analysed.

The monitoring system is preferably configured to periodically detect whether the mandibular repositioning device is in use or not, the result of this detection being recorded in a recorder of the monitoring system. When it is needed to assess the compliant use of the mandibular repositioning device, it is then possible to transfer the recorded data to the processing system. This can be accomplished by returning the mandibular repositioning device to the provider of the device or providing the user with a suitably configured communication device that receives recorded data from the monitoring system and forwards the data to the provider of the device. When communicatively coupled to a suitably configured communication device, the monitoring system receives commands that dictate such monitoring system to transmit the recorded measurements. The transmitted measurements can be used to determine whether the user of the mandibular repositioning device has complied with a recommended usage schedule.

The communication device is part of a processing system that further comprises an analysing device. Therefore, the communication device is usually used to retrieve the information recorded within the monitoring system, and such retrieved information is then transmitted to the analysing device. Such analysing device thus identifies, collects and organises the information from the monitoring system via the communication device in order to determine and report compliant or non-compliant use of the mandibular repositioning device. The processing system not only collects and organises the information to determine compliant use, but provides an interface to the practitioner, the patients and any people to communicate with each other and view one or more reports that compare the patient's use with the prescribed use and possibly compare the patient's use with other patients using similar mandibular repositioning devices.

Figure 2:
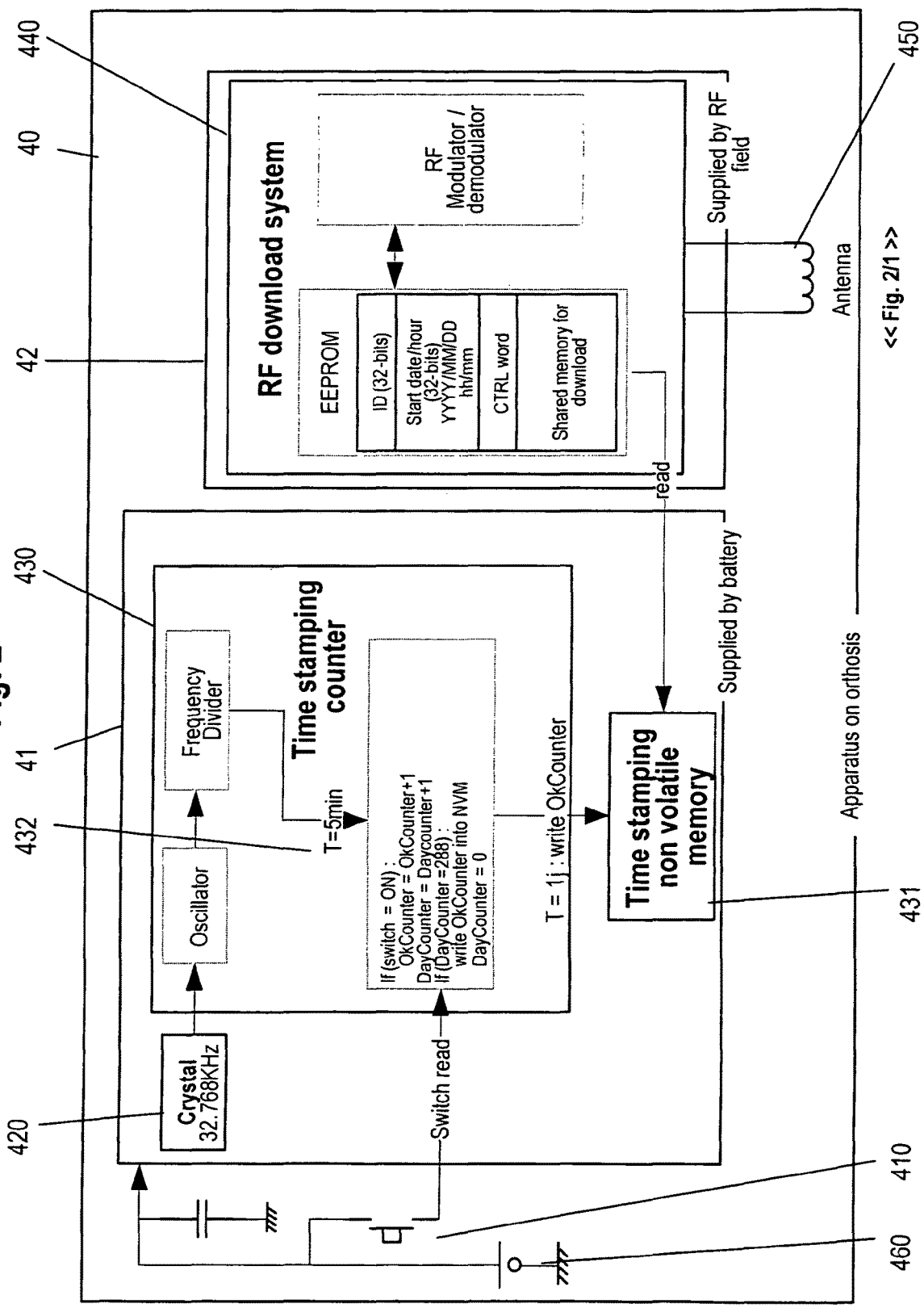
FIG. 2 is a representation of an apparatus for determination of compliant use of an intraoral orthosis.

FIG. 2 schematically illustrates the general structure and components of the apparatus for determination of compliant use of a mandibular repositioning device. The main component of this apparatus is the monitoring system 40 which is to be coupled to the mandibular repositioning device, and which comprises two main assemblies, that is a detection assembly 41 for detection of the use of the mandibular repositioning device and storage of the corresponding data, and a communication assembly 42 for transmission of the recorded data to the remote communication device 50.

Such monitoring system 40 first comprises a detector 410, part of the detection assembly 41, provided for detecting whether the mandibular repositioning device is in use or not. It is preferable that this detector 410 operate as a switch, which is switched on when the mandibular repositioning device is in used, and switched off when the mandibular repositioning device is not used. Thus the detector 410 provides measurement data that inform on whether the mandibular repositioning device is in use or not.

The detection assembly 41 of the monitoring system 40 further comprises a clock 420 for associating the detected measurement data on use or not of the mandibular repositioning device with time information data, that is the time at which the detection has been made, like a timestamp of the measurement data.

The detection assembly 41 of the monitoring system 40 may comprise a recorder 430 for recording the detected measurement data and the corresponding time data. Such measurement and time data may be recorded as raw data directly in a storage medium 431, like for example an erasable programmable non volatile memory (EEPROM, FRAM or Flash memory) or any other computer readable medium suitable to store data. Alternatively, the measurement and time data may be slightly processed within the monitoring system 40 by a suitable processor 432, so as to store less data in the storage medium. For instance, instead of storing the raw data on use and corresponding measuring time, the monitoring system 40 may be programmed to store processed data corresponding for instance to the accumulated period of time per day the mandibular repositioning device has been used or not. Most preferably the monitoring system 40 may be programmed to either store raw data which is very advantageous for use in clinical trials where precise data is required, or programmed to store processed data preferably for use in clinical practice to preserve patient privacy. To this end, the processor 432 is programmable, and is preferably remotely programmable via the communication assembly 42 for example.

The monitoring system 40 further comprises a transponder 440, part of the communication assembly 42, that enables communication of data between the monitoring system 40 and the communication device 50. Preferably, the transponder 440 is connected to the recorder 430 so as to read and download the measurement and time data of the storage medium 431 of the recorder 430, for further communication with the communication device 50 via a communication component 441. The transponder 440 further comprises a storage medium 442 that is used to store the data relating to the identification of the mandibular repositioning device, data relating to the start time of the detection (so as to correlate this start time information with the information from the clock in order to get a precise timestamping of the measurement data), and data referred as the CTRL word for controlling operation of the transponder. Preferably, the storage medium 442 of the transponder 440 may also be used as a buffer for transmission of data from the storage medium 431 of the recorder 430 to the communication device 50.

Preferably, communication between the transponder 440 and the communication device 50 is wireless, such that the communication assembly 42 of the monitoring system 40 further comprises an antenna 450 connected to the transponder 440. Most preferably, the communication assembly 42 is adapted for radiofrequency communication with the communication device 50, in which case the transponder 440 may be a radiofrequency identification (RFID) tag, having an RFID modulator/demodulator as communication component 441 and an EEPROM as storage medium 442.

Finally, the monitoring system 40 comprises an integrated power supply 460, like a battery, which is used for providing power to the components of the detection assembly 41. The communication assembly 42 is preferably powered by a remote power feeding from the communication device 50 through the antenna 450, in which case the transponder 440 may be a passive RFID tag (also called RFID transponder). In an alternative arrangement (not shown) the transponder 440 may send the measured data in real-time to the communication device 50 such that a recorder is not required within the monitoring device. In a further alternative arrangement (not shown), the data may be transferred using a wired system. In such an arrangement, when data is to be communicated to the communication device 50, a wire or cord is coupled between the communication device and the monitoring system 50. Preferably the monitoring system 40 includes a connector adapted to receive a plug of the wire or cord for coupling to the communication device 50. Preferably a cover or seal may be located over the connector in the monitoring system 50 to protect the connector from contamination when located within the mouth. Preferably the monitoring system is removed from the patient's mouth for coupling to the communication device 50.

The communication device 50 is used for sending information to the monitoring system 40, for instance when configuring the monitoring system 40 for first use (identification of the mandibular repositioning device, start time of the detection). Most importantly, the communication device 50 is adapted for retrieving information (in particular measurement data and corresponding time data) recorded by the monitoring system 40.

To this end, the communication device 50 may for instance comprise an interrogator 510 adapted for retrieving the information contained within the monitoring system 40, and also for sending configuration data. In case the monitoring system 40 comprises a RFID tag 440, then the interrogator could be a RFID interrogator 510 (also called RFID transceiver). In addition to the emission and reception of data between the RFID interrogator 510 and the RFID tag 440, the radiofrequency field may be used to provide power from the communication device 50 to the monitoring system 40 through the RFID interrogator 510 and RFID tag 440.

The communication device 50 further comprises a microcontroller 520 that is used to drive the interrogator 510 in retrieving the data recorded in the monitoring system 40. Such microcontroller 520 is also used to manage the data received from the analysing device 60 of the processing system. Communication between the communication device 50 and analysing device 60 may be wireless or wired, with for instance a USB. ZigBee, Bluetooth connection or any other suitable connection.

The communication device 50 may further comprise display means 530 for providing simple information to the user on the compliant use of the mandibular repositioning device. For instance, it may provide very general information of the use of the mandibular repositioning device like the accumulated period of time during which the patient has used the device since the start time indicated in the monitoring system 40.

Information on the identification of the mandibular repositioning device may also be provided through the display means 530 of the communication device 50.

The communication device 50 may comprise an integrated power supply like a battery, or may be supplied by an external power supply 540 as illustrated on FIG. 2.

Finally, the apparatus for determination of compliant use of a mandibular repositioning device preferably comprises an analysing device 60 which is in communication with the communication device 50 as mentioned above.

Such analysing device 60 is first used by the provider of the monitoring system 40 to configure such monitoring system 40, for example in identifying the mandibular repositioning device, instructing for the monitoring system 40 to start detection (start time point), and possibly erase the data previously recorded in the monitoring system 40.

The analysing device 60 is also used for retrieving the data recorded in the monitoring system 40 through the communication device 50 for storing such data, and possibly further processing them for analysis of the compliant use of the mandibular repositioning device by the patient.

The analysing device 60 may for instance be a computer adapted for processing data, storing data, and displaying raw or processed data to a user.

Electronic Structure and Operation of a Preferred Monitoring System

As mentioned above, the main function of a preferred monitoring system 40 is to periodically detect whether or not the mandibular repositioning device is in use by periodically checking the state of a switch detector (e.g. switched on when the device is in use, and switched off when the device is not in use).

Each of the measurement data from the periodical detection is associated with time data, like a time stamp of the measurement data.

These data may be stored as raw data (for instance when a detailed analysis of the compliant use of the mandibular repositioning device has to be made), or slightly processed so as to store less data and thus enable a longer operation of the monitoring system without external intervention.

Preferably, the monitoring system 40 is designed so as to enable retrieve of recorded data by the communication device 50 even in case of breakdown or failure of the power supply 460.

The corresponding electronic structure could be specifically designed in an application-specific integrated circuit (ASIC). Use of an ASIC is advantageous in terms of power consumption but its specific development is very expensive.

Figure 3:
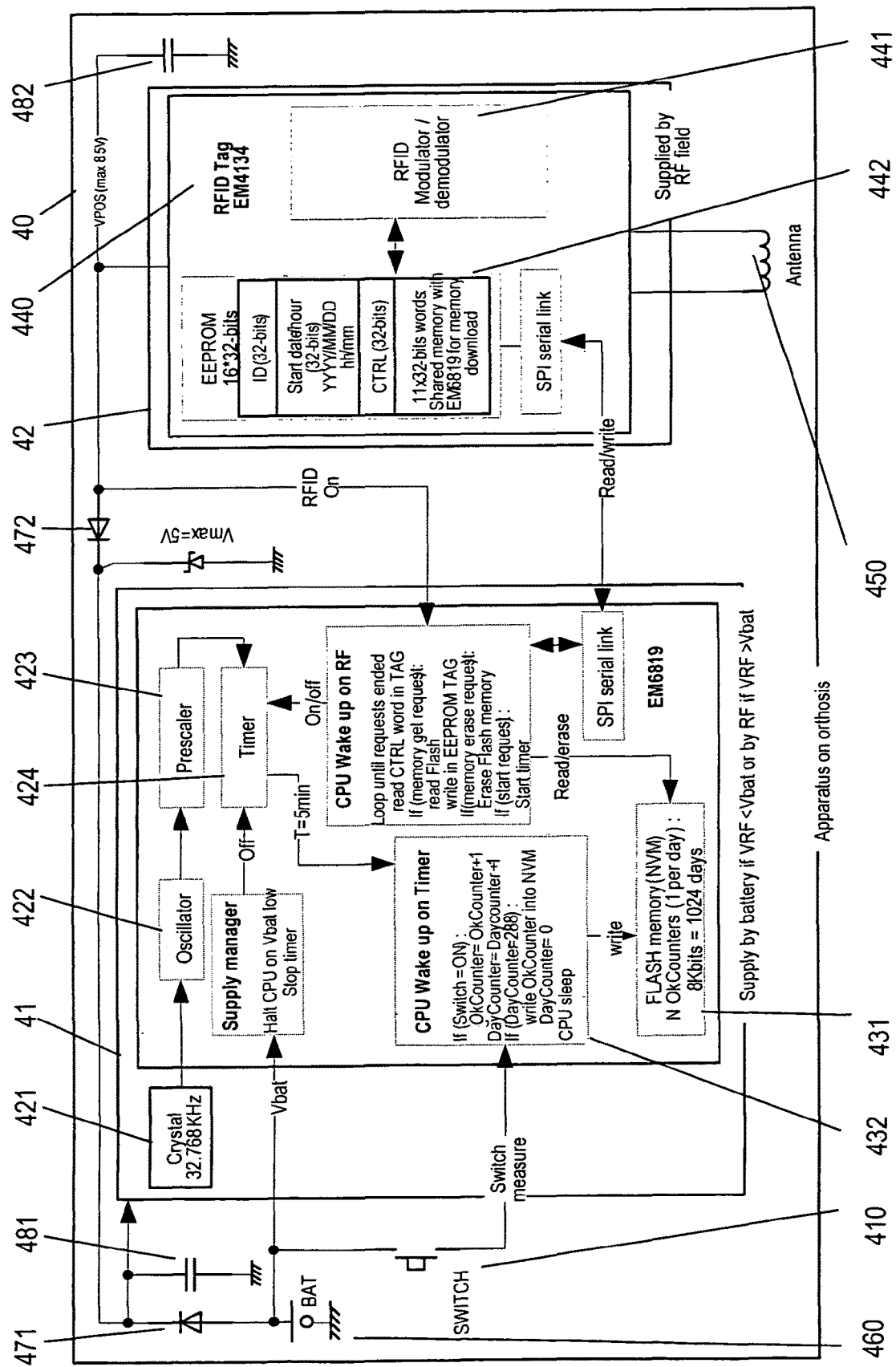
FIG. 3 is a representation of an electronic architecture of a monitoring system for the apparatus for determination of compliant use of an intraoral orthosis of FIG. 2.

A cheaper alternative is thus to design an electronic architecture of the monitoring system with existing electronic components available on the shelve. FIG. 3 illustrates a preferred electronic architecture for the monitoring system 40 that we will now describe in detail.

An arrangement that limits the number of components within the monitoring system 40 is to provide a flexible PCB (printed circuit board) comprising a battery 460, a switch detector 410, an antenna 450, two integrated circuits provided respectively for the detection assembly 41 and the communication assembly 42, and two diodes (471;472) and two capacitors (481;482).

The first integrated circuit provided for the detection assembly 41 is preferably a microcontroller 41 connected to the battery 460 for being power supplied. It is further connected to the switch detector 410. Preferably, the microcontroller 41 includes at least the following:
 a central processing unit (e.g. 4-bit or 8-bit processor);
 a clock generator (often an oscillator for a quartz timing crystal, resonator or RC circuit);
 discrete input and output bits, allowing control or detection of the logic state of an individual package pin;
 serial input/output such as serial ports and other serial communications interfaces like Serial Peripheral Interface (SPI);
 peripherals such as timers, prescalers, event counters, and watchdog;
 volatile memory (RAM);
 non volatile memory ROM, EEPROM, FRAM or Flash memory;
 in-circuit programming and debugging support.

The monitoring system 40 of the invention may for example comprise the microcontroller referenced EM6819 commercialised by EM Microelectronic-Marin SA, which is an ultra low power 8-bit flash microcontroller which comprises at least the following components:
 an internal oscillator 422 (internal RC oscillator, 2 MHz and 15 MHz pre-trimmed, and internal oscillator for an external low frequency crystal 421 e.g a 32768 Hz crystal);
 a prescaler 423;
 an 16-bits timer 424;
 serial input/output and Serial Peripheral Interface (SPI);
 an wake-up system 432 associated to internal events from timer, inputs/outputs, and/or SPI;
 a 16.9 kByte shared General Purpose Non Volatile Flash memory 431 (with max 6 kByte Instructions program memory and max 12 kByte non volatile data memory).

The second integrated circuit provided for the communication assembly 42 is an integrated circuit for use as an electronic Read/Write radiofrequency transponder, also called an RFID tag 440. In addition to a RFID modulator/demodulator 441, this RFID tag 440 should comprise a memory 442 (like a 16×32 bits EEPROM) for storing data such as the identification number, the start time and the CTRL word, but also for operating as a buffer between the storage medium 431 of the detector assembly 41 and the communication device 50. Preferably, the RFID tag 440 is adapted for a direct connection of the antenna 450 thereon.

The monitoring system 40 may for example comprise the RFID tag referenced EM4134 commercialised by EM Microelectronic-Marin SA, which operates at 13.56 MHz and comprises an EEPROM of 512 bits organised in 16 words of 32 bits. Further this RFID tag comprises SPI ports so that it may be easily connected to the microcontroller 41 for exchanging data.

In addition to these integrated circuits, the monitoring system 40 comprises a first diode 471 positioned serially after the battery 460 so as to protect such battery 460 when the voltage generated by the radiofrequency field is higher than the battery voltage. It also comprises a second diode 472 positioned between the RFID Integrated circuit 42 and the microcontroller 41 so that the microcontroller 41 can be powered by the RFID integrated circuit 42 when the RFID communication is active.

Finally, the monitoring system 40 comprises two capacitors (481;482) that are positioned as bypass capacitors in order to filter the power supply of the microcontroller 41 and RFID tag 42 respectively.

For this specific architecture, a 3 Volts battery is required (or two 1.5 Volts batteries). A Lithium based battery with a capacity of 25 mAh may for instance be used for the monitoring system 40, such battery being used for supplying power to the microcontroller 41.

The above architecture of the monitoring system 40 enables reducing the power consumption at the minimum. Indeed, the microcontroller 41 of the detection assembly is generally in a sleep state where the processor is halted. When a detection is required, then an interrupt from the timer wakes the microcontroller 41 up, and the state of the switch detector 410 is checked.

The interruption is launched periodically (for instance each 5 minutes) through cooperation of the crystal 421, oscillators 422, prescaler 423 and timer 424. As the sleep state has been interrupted, the processor of the microcontroller 41 is powered and checks the state of the switch detector 410. If this switch detector 410 is closed, which means that the mandibular repositioning device is in use, then a temporary counter data (for example stored in the RAM of the microcontroller 41) is incremented. After a 24 hours period of time, the data of the temporary counter is recorded in the non volatile memory of the microcontroller with a corresponding data on said period of time. Alternatively, the measurement data from the switch detector 410 might be directly recorded in the non volatile memory such that a very detailed analysis of the compliant use of the mandibular repositioning device could then be made.

Retrieve of the recorded information in the non volatile memory of the microcontroller is made by activating the RFID tag 42 with the communication device 50. The RFID tag 42 and microcontroller 41 are connected together so that a voltage from the RFID tag 42 may interrupt the sleep state of the microcontroller 41 to launch another procedure of the microcontroller. This procedure acts as a protocol decoder in order to launch different requests from the interrogator through the control word (referred to the CTRL word) located in the EEPROM memory 442. In particular, one of these requests is adapted so that the data stored in the non volatile memory of the microcontroller 41 is progressively transferred to the communication device 50 via the EEPROM of the RFID tag 42 which operates as a buffer.

In case of breakdown or failure of the battery 460 provided in the monitoring system 40, the detection assembly may no longer be activated for periodical detection of the use of the mandibular repositioning device. The proposed electronic architecture however still enables retrieving the data recorded in the EEPROM of the microcontroller 41 as the RFID tag 42 may be used to supply power to the microcontroller 41.

This is very advantageous, in particular because the battery provided in the monitoring system 40 is generally not changeable or reparable. The monitoring device may also comprise a re-chargeable battery, more preferably a battery chargeable by induction. Further, retrieve of data is made wirelessly without degradation of the mandibular repositioning device nor of the monitoring system.

In addition to the possibility to retrieve the recorded data even in case of breakdown of the battery, the above electronic architecture comprises several further advantages.

In particular, such architecture may be implemented with very common and available electronic components. This thus ensures that the proposed solution is not dependent on a particular component. Moreover, the proposed solution requires few electronic components.

Further, programming of the microcontroller is easy and could be performed with common computer languages raising no technical difficulty.

It also thus appears that the proposed solution is very cost effective, in terms of development and production costs.

Finally, the proposed electronic architecture enables the monitoring system 40 to be used during a long period of time (approximately 3 years for the specific solution described above) without any maintenance or any other human intervention.

Preferred Method of Detection of the Compliant Use of the Mandibular Repositioning Device The switch detector 410 used in the proposed preferred monitoring system 40 operates as an interrupter. More precisely, when a tooth is detected by the detector 410 which means that the mandibular repositioning device is in use, then the interrupter is switched ON and the temporary counter of use of the mandibular repositioning device is incremented by the corresponding period of time. If no tooth is detected, then the interrupter remains switched OFF such that the temporary counter is not incremented.

The switch detector 410 may be a pressure detector which is switched ON when being pressurized in an oral cavity, e.g. when in contact with a tooth. More specifically the switch detector may consist in a membrane switch arranged so as to be positioned facing the teeth. A membrane switch is a thin, low-profile, micro-motion, front-panel assembly with one or more layers of polyester. Screen-printed conductors are printed on each layer and pressure-sensitive adhesives are used to bond the polyester layers together.

However, the switch detector 410 is preferably an optical detector enabling detection of the compliant use of the mandibular repositioning device without contact with the teeth. Therefore, there is no risk of damaging the teeth of the patient because of the monitoring system, nor any risk of discomfort because of that monitoring system coming against the teeth.

More precisely, the switch detector 410 preferably used in the monitoring system 40 consists in a reflective optical detector, that is a component provided both with a light emitter for emission of light, and corresponding light receiver for detection of light, as is illustrated in FIG. 5. Operation of such a switch detector is thus based on the reflection of light on a component. This reflective optical detector most preferably operates in the infra-red (IR).

Providing a reflective infra-red detector is very advantageous for the following reasons. First, the fact that the switch detector operates both as the IR emitter and the IR receiver enables having a very compact monitoring system 40 as all the electronic components may be positioned on a single PCB, without having a need to deport the emitter away from the receiver which would make the integration and fixation of the monitoring system within the mandibular repositioning device much more complex. We will come back on this aspect below when considering the coupling of the monitoring system with the mandibular repositioning device.

Providing a reflective detector which operates with infra-red is further advantageous as this enables limiting, or even preventing, any influence of ambient or artificial light in the detection process. First the fact that the receiver is adapted for detection of IR signals naturally limits the influence of ambient or artificial light which wavelength is generally not within the infra-red spectrum and which should thus not be detected. It is further possible to reduce or fully preclude the influence of ambient or artificial light by detecting the variation of the detected signal with and without emission of an IR signal and then correlate this variation with the emitted IR signal.

Preferably, the reflective IR detector used for the monitoring system has an optimal operating distance comprised between 1 mm and 5 mm. The reflective IR detector is thus preferably positioned along one of the two opposite walls of the splint (preferably the lower splint) of the mandibular repositioning device. Most preferably, the reflective IR detector is positioned along the external wall of the lower splint, so as to ease the integration of the monitoring system within the oral appliance without causing discomfort for the patient. This small operating distance of between 1 mm and 5 mm prevents the emitted IR signals to be reflected by the opposite wall of the corresponding splint of the mandibular repositioning device.

As is illustrated in FIG. 5, a preferred mandibular repositioning device is in position in the mouth of the patient, with the lower and upper splints respectively around the lower and upper teeth 70. The signal, preferably an IR signal, emitted by the reflective detector 410 of the monitoring system 40 may be reflected onto the teeth 70, tissue inside of the cheek and/or gum and thus be detected by this reflective detector 410. A preferred advantage in the use of IR signal is that its wavelength may be adapted for optimal reflection on the teeth enamel, tissue inside of the cheek and/or gum. It could even be contemplated to adjust the wavelength of the IR signal to the particular teeth enamel of the patient or particular gum colour of the patient, by calibrating the monitoring system prior to its first use by the patient.

According to other preferred embodiments, as discussed above, the monitoring system, preferably the detector, is adjustable, e.g. by changing or varying physical parameters, based on a particular property or characteristic of a patient or group of patients. Different types of detectors, preferably sensor(s) and emitters may be used, as referred to above.

Figure 4:
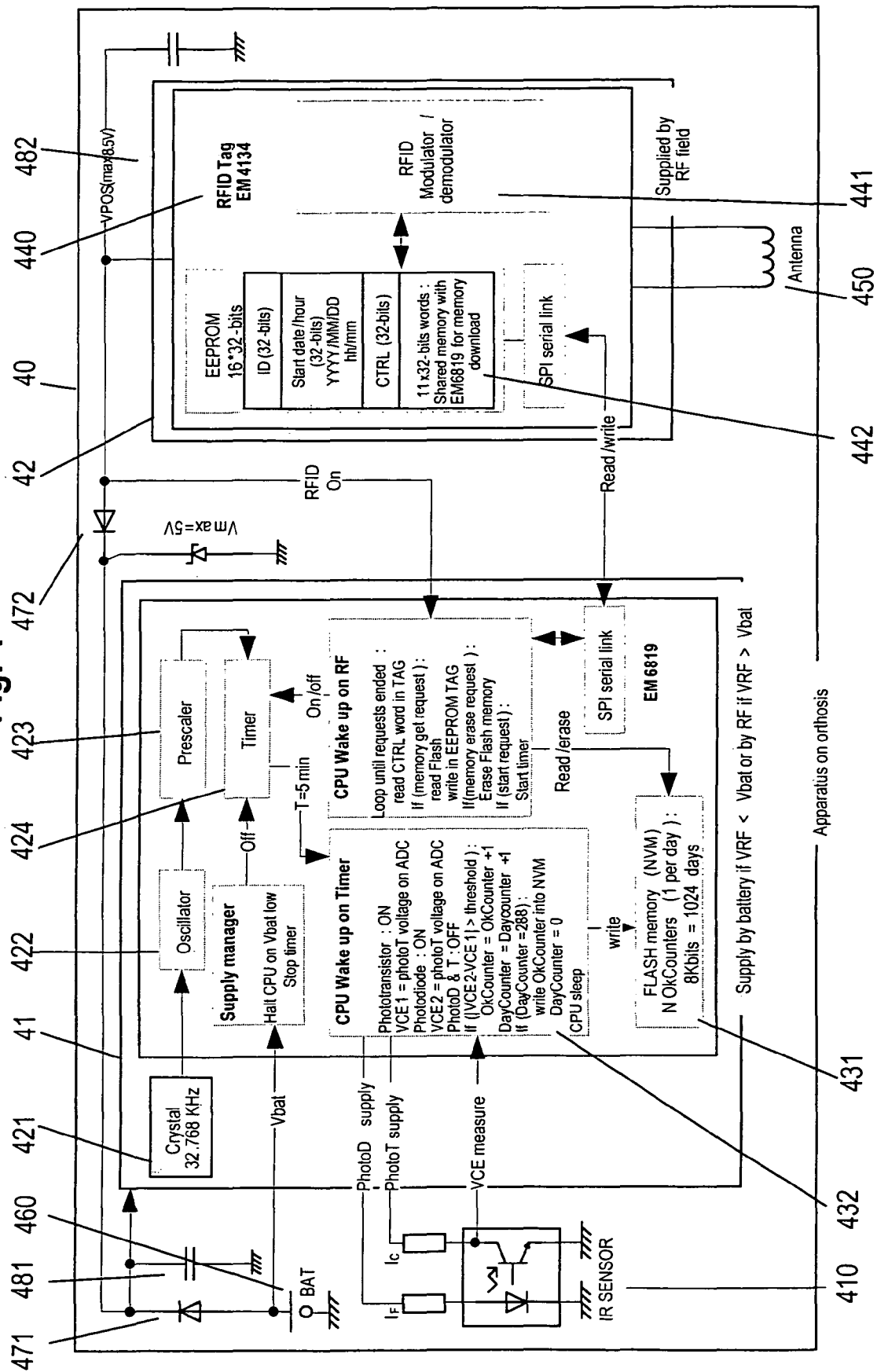
FIG. 4 is a representation of an electronic architecture of a monitoring system with a reflective infra-red detector.

This is particularly advantageous as this increases the reliability of the detection method which cannot be tricked by the patient intentionally or unintentionally. In particular, as the signal, preferably IR signal is adjusted to, e.g., the particular teeth enamel of the patient or particular gum colour of the patient, the mandibular repositioning device will not be considered in use when simply put on a dental cast of the teeth of said patient, said dental cast being generally made of plaster. FIG. 4 illustrates a preferred electronic architecture of a monitoring system 40 that integrates a reflective IR detector 410.

The preferred operation of such a monitoring system 40 is similar to what has been described above. Then each time the interruption routine is launched by the timer 424 of the detection assembly 41, the reflective IR detector is activated and programmed to operate two successive measures. The first measure $V_{CE1}$, which is not compulsory but preferable, is made to eliminate the influence of ambient or artificial light that could also be detected by the reflective detector. For the second measure $V_{CE2}$, an IR signal is emitted by the reflective IR photodiode such that the reflective detector measures the reflected IR signal if any. To this end, the first measure is made without emission of an IR signal such that the detected signal necessarily corresponds to noise, especially from ambient or artificial light.

Then, the corrected measure corresponding to the difference between the first and second measure is compared to a threshold value, which determines whether a tooth is detected (corresponding to an ON state of the switch detector, meaning that the mandibular repositioning device is in use) or not (corresponding to an OFF state of the switch detector, meaning that the mandibular repositioning device is not in use).

Hereafter, exemplary, non limiting embodiments and functionalities of signal emitter and a signal receiver, here a preferred IR light emitter and IR light receiver, are described more in detail. However, other preferred embodiments with a different detector, and/or differing functionalities or algorithms may be used.

The proposed monitoring system may for instance integrate a reflective IR detector of the SFH9201 series from company OSRAM Opto Semiconductors (reference SFH9201, SFH9201-½, SFH9201-⅔ or SFH9201-¾ depending on the sensitivity of the receiver).

The features of such detector are the following:
operating distance from 1 mm to 5 mm;
IGaAs-Diode as IR emitter in combination with a silicon NPN phototransistor as IR receiver;
Daylight cut-off filter against undesired light effects;
$I_{Fmax}$=50 mA, $I_{Fnom}$=3-20 mA (forward current of the emitting diode),
$I_{CE}$=0.63-2 mA for $I_F$=10 mA (sensitivity of the receiver for reference SFH9201-¾),
Wavelength of the emitter: 950 nm+/−50 nm (IR),
Wavelength of the receiver: 900 nm+/−150 nm.

Preferably the reflective IR detector 410 comprises one IR light emitter adapted to emit infrared light and one IR light receiver adapted to receive infrared light. The IR light emitter and IR light receiver operate with IR light, preferably with a wavelength in the range of 800 nm-1100 nm, most preferably in the range of 900 nm-1000 nm, such as about 940 nm, 950 nm or 960 nm. The reflective IR detector could be any adjustable IR detector which may be adjusted in the above or below described manner, for instance, the KTIR0711 produced by KingBright or the SFH9201 series from OSRAM Opto Semiconductors. The emitted IR light, preferably a polarized light, is reflected at the tooth or teeth and the reflected light is then received by the IR light receiver. E.g. the wavelength and/or intensity of reflected IR light received by the IR light receiver may vary from the wavelength and/or intensity of the emitted IR light.

The properties of the signal received may, inter alia depend on:
the properties of the signal emitter and/or signal receiver;
at least one particular property of a patient or a group of patients, such as
the geometrical relationship between the signal emitter, signal receiver and/or the reflecting object, for instance the tooth or teeth or gum or inside of the cheek;
the properties of the reflecting object; and/or
environmental conditions.

More specifically, the properties such as intensity of received light measured at the IR light receiver and/or its wavelength may, inter alia, vary depending on one or several of the following aspects:
the amount of light emitted by the IR light emitter which is preferably controlled by the supply voltage and/or the current of the IR light emitter which is converted to the emitted light;
the encapsulation of the IR light emitter and/or the IR light receiver;
at least one particular property of a patient or a group of patients, such as
the relative position, e.g. the distance(s) and angle(s) between the IR light emitter, the IR light receiver and/or the tooth or teeth or gum or inside of the cheek;
the geometry of the tooth or teeth or gum or inside of the cheek of the patient, on which the light is reflected;
the reflection characteristics the tooth or teeth or gum or inside of the cheek of the patient, on which the light is reflected, particularly of the tooth enamel, more particularly the surface properties like reflectiveness and/or color;
the type of tooth or teeth, for instance, a natural, ceramic and/or gold tooth or teeth;

the noise, for instance, caused by ambient or artificial light not being emitted by the IR light emitter; and/or the fluid media in contact with the emitted and/or reflected light such as, for instance, saliva and/or ambient air.

The intensity of the light received by the IR light receiver is preferably measured by measuring the voltage drop at the IR light receiver which inter alia depends on the supply voltage of the IR light receiver, the resistance associated with the IR light receiver and the current related to the received and converted light.

Preferably, the sensitivity of the IR light receiver is adapted by the variation of at least one resistor associated with the IR light receiver and/or IR light emitter. In other words, the IR light receiver and/or IR light emitter, thus the reflective optical detector 410, is tuned as regards the capability to detect a variance in the received light vis-à-vis the emitted light.

The current of the IR light emitter and the voltage drop of the IR light receiver may be set by at least two resistors. Preferably, the current $I_F$ of the IR light emitter and/or the voltage drop at the IR light receiver are set by a resistor $R_F$ in series with the IR light emitter and a resistor $R_C$ associated with the IR light receiver, respectively. Preferably in accordance with the equations:

$$I_F = (V_{SUPPLY} - V_{DIODE})/R_F \quad (1)$$

and $$V_{CE} = V_{SUPPLY} - R_C \times I_C, \quad (2)$$

wherein:
$I_F$ is the current of the IR light emitter;
$V_{SUPPLY}$ is the supply voltage of the IR light receiver and/or the IR light emitter;
$V_{DIODE}$ is the voltage at the IR light emitter;
$R_F$ is a resistor, e.g. in series with the IR light emitter;
$V_{CE}$ is the voltage at the IR light receiver;
$R_C$ is a resistance at the IR light receiver;
$I_C$ is the current $I_C$ at the IR light reciever.

Equations (1) and (2) indicate that with decreasing resistance $R_F$, current $I_F$ and thus the IR light emission increases, and that with increasing resistance $R_C$, the variation of the voltage $V_{CE}$ at the IR light receiver and thus the sensitivity of the measured signal of the IR light receiver, the IR flux reflection sensitivity, increases.

The monitoring system 40, preferably the PCB, may comprise at least one resistor, preferably several resistors, with different resistances. The PCB may comprise, for instance, resistors R1 to R5. They may be selectable by software, for instance by at least one signal, for instance signals IF0, IF1 and IC0, IC1, IC2. Preferably the resistors may be selectable in an alternative or cumulative fashion. The several resistors may be used together in at least one combination, preferably in all combinations, as discussed before.

Preferably, the noise caused by ambient and/or artificial light contained in the light received by the IR light receiver is reduced, preferably precluded. During a period of time, preferably when the monitoring system 40 is applied in the oral cavity, only the ambient and/or artificial light is measured by the IR light receiver without light being emitted from the IR light emitter.

As shown in FIG. 4, a procedure for determining compliant use may comprise at least one of the following steps:
applying a voltage to the resistor $R_c$ at a IR light receiver, here configured as a phototransistor;
measuring the received light caused by ambient and/or artificial light by measuring the voltage $V_{CE}$ and set the measured value as $V_{CE1}$;
applying also a voltage to the resistors $R_F$ connected in series to the IR light emitter, here configured as a photodiode;
measuring the received light by measuring the voltage $V_{CE}$ and set the measured value as $V_{CE2}$;
calculate the difference delta $V_{CE}$ which represent the received light without the influence of ambient and/or artificial light with the equation:

$$\text{delta } V_{CE} = V_{CE2} - V_{CE1}; \text{ and} \quad (3)$$

compare the difference delta $V_{CE}$ to a preset threshold value $V_T$.

If the difference delta $V_{CE}$ is larger than the threshold value $V_T$ then a tooth is in front of the sensor and thus a compliant use may be assumed. The counter or counters indicating the compliant use time may then be incremented or any other data indicative for the compliant use time may be stored. If the difference delta $V_{CE}$ is not larger than the threshold value $V_T$, the compliance monitor may assume that the device is not worn, worn on a fake apparatus, or worn by someone else. After the measurements and evaluations the phototransistor, the photodiode, and/or the microcontroller may be switched off or switched to a sleep mode, preferably until a wake up signal, for instance by a timer, triggers the next determination procedure.

Figure 10:
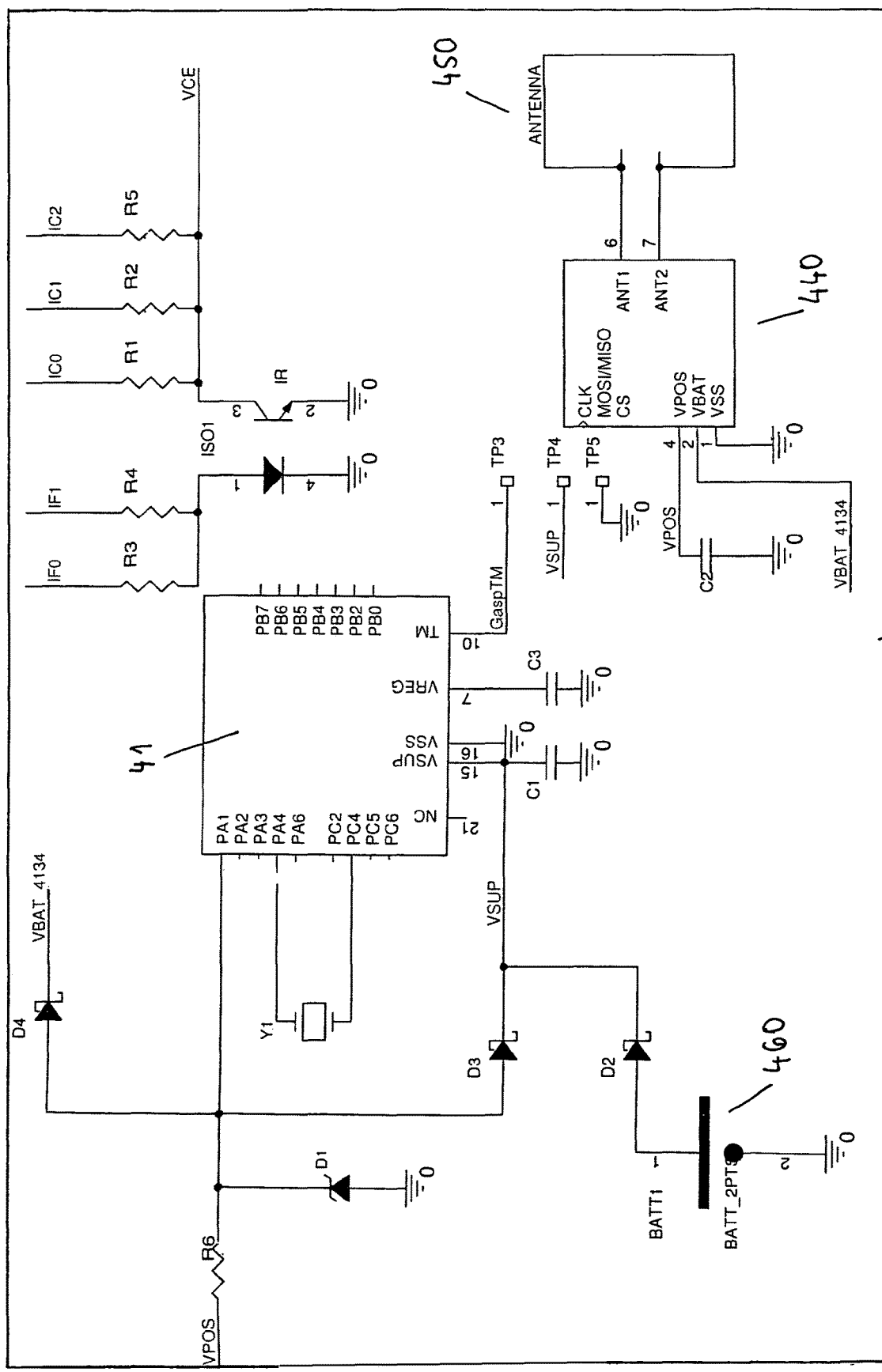
FIG. 10 is a schematic extract of an electronic architecture of a monitoring system with a reflective infra-red detector.

As shown in FIG. 10, exemplary and preferred only with the detector 410 being an IR detector, the resistance $R_c$ may be selected from the resistors $R_1$, $R_2$, or $R_5$ or any combination thereof, thus leading to 7 possible combinations. The resistance $R_F$ may be selected from the resistors $R_3$ or $R_4$ or any combination thereof, thus leading to 3 possible combinations. With the resistors $R_1$, $R_2$, or $R_5$ for $R_C$, and $R_3$ or $R_4$ for $R_F$, in total 3×7=21 possible combinations of resistances may be selected. The respective resistors' pins of the microprocessor may be selected for the resistance $R_C$ and the resistance $R_F$ using the signals IC0, IC1, IC2 and IF0, IF1, respectively.

A preferred or ideal combination of the resistances for $R_C$ and $R_F$ may be the result of a calibration or tuning described hereafter. Moreover, also the threshold value $V_T$ may be the result of a calibration or tuning step.

With afore-mentioned different combinations of the resistances $R_C$, $R_F$, here 21 combinations, a certain number of differences delta $V_{CE}$, here 21, may be obtained in accordance with above equations 1 to 3. A sample measurement of the difference delta $V_{CE}$, preferably a multitude of sample measurements, for instance 32 sample measurements, may be carried out for at least some, preferably each, possible combinations of resistances in different setups.

A first set of sample measurements may be taken, as in the shown embodiment, 32 sample measurements of the difference delta $V_{CE}$ for each of the 21 possible combinations $R_C$, $R_F$ of the resistances R1 to R5 may be taken and stored for a configuration or setup without any tooth in front of the intraoral appliance. Moreover the average values delta $V_{CE\ average\ without}$, for instance 21 values delta $V_{CE\ average\ without}$, may be calculated out of the 32 samples measurements for each of the 21 combinations of the resistances R1 to R5 for the first set of sample measurements.

In the same way, a second set of sample measurements may be taken, stored and processed in a setup with a tooth in front of the intraoral appliance leading to, inter alia, 21 average values delta $V_{CE\ average\ with}$.

A difference between the average values delta $V_{CE}$ of the second setup, namely delta $V_{CE\ average\ with}$, and the average values delta $V_{CE}$ of the first setup, namely delta $V_{CE\ average\ without}$ may be calculated, for instance, for each possible combination $R_C$, $R_F$ in accordance with the equation:

$$\text{delta delta } V_{CE\ x} = \text{delta } V_{CE\ average\ with\ x} - \text{delta } V_{CE\ average\ without\ x} \quad (4)$$

wherein
- delta $V_{CE\ average\ without\ x}$ is the average value for delta $V_{CE}$ of the first setup without a tooth in front of the intraoral appliance for a given combination x of the resistances $R_C$, $R_F$; and
- delta $V_{CE\ average\ with\ x}$ is the average value delta $V_{CE}$ of the second setup with a tooth in front of the intraoral appliance for a given combination x of the resistances $R_C$, $R_F$;
- x is the polarization number representing the different combinations of the resistances $R_C$, $R_F$; $1 \leq x \leq 21$.

A preferred or ideal combination or adjustments of the resistances for $R_C$ and $R_F$ is the combination of $R_C$ and $R_F$, here expressed by x, for which delta delta $V_{CE\ x}$ has its maximum value. With the preferred or ideal combination or adjustments of the resistances $R_C$ and $R_F$ the threshold value may be calculated to $$V_T = (\text{delta } V_{CE\ average\ with\ xp} + \text{delta } V_{CE\ average\ without\ xp})/2 \quad (5)$$

wherein
- delta $V_{CE\ average\ without\ xp}$ is the average value delta $V_{CE}$ of the first setup without a tooth in front of the intraoral appliance for the preferred adjustments of the resistances $R_C$, $R_F$;
- delta $V_{CE\ average\ with\ xp}$ is the average value delta $V_{CE}$ of the second setup with a tooth in front of the intraoral appliance for the preferred adjustments of the resistances $R_C$, $R_F$; and
- xp is the polarization number of the combination of resistances $R_C$, $R_F$ being the preferred adjustments of the monitoring device.

Moreover, the margins may be checked by considering delta $V_{CE\ average\ with\ xp} - V_T$ and $V_T -$ delta $V_{CE\ average\ withour\ xp}$. A preferred, exemplary correct value for the margins is 40 for both.

Any of the afore-mentioned steps, such as the compliance monitoring steps, the steps for adjusting the resistors, selecting the preferred adjustments of the resistors, setting the threshold value $V_T$ and/or the margins may be done automatically. A step may be launched by the monitoring device, the communication device and/or the analysing device, preferably from a request of the radiofrequency reader. The tuning or adjustment is preferably performed by a physician and may be repeated in certain intervals.

Mechanic Structure of the Monitoring System

The different electronic components needed to perform the required functions of the monitoring system are arranged to form an element as compact as possible, so that the monitoring system may be easily coupled to the mandibular repositioning device. The specific electronic architecture proposed above is of particular interest for manufacturing a very compact monitoring system, but other electronic architectures that fit the compactness requirement may also be contemplated.

The monitoring system proposed for assessing the compliant use of the mandibular repositioning device is namely preferably manufactured as a distinct element from the mandibular repositioning device, adapted to be coupled with such device for detection of use or not of the device by the patient. Consequently, the different electronic components of the monitoring system are preferably arranged on a single PCB (preferably a flexible PCB so that the antenna may be manufactured directly of the PCB, by etching for example) which is then encapsulated with a biocompatible material. Such arrangement thus forms a distinct element that may for instance be plugged on the mandibular repositioning device at a location chosen for not hurting the patient, or plugged in a cavity provided in the mandibular repositioning device which ensures not causing discomfort or pain to the patient.

FIGS. 6a and 6b illustrate a possible arrangement for the components of the monitoring system 40 proposed above with a reflective IR detector. More precisely, there is provided a flexible PCB 490 onto which are arranged a battery 460, a reflective IR detector 410, a RFID tag 42, and a microcontroller 41 with its external crystal 421. The antenna 450 is then etched on the flexible PCB, preferably at an end of the PCB to be as far as possible from the battery in order to limit interferences.

FIGS. 7a and 7b illustrate the arrangement of FIGS. 6a and 6b being encapsulated in an appropriate biocompatible material 500 to form the monitoring system 40 to be coupled to the mandibular repositioning device. Preferably, the over-moulding is made with a biocompatible epoxy resin, compatible with the moulding of electronic components and which has optical properties adapted for IR detection. Depending on the transparency to IR of the biocompatible material, the portion of the over-moulding facing the reflective IR detector may be processed so that the encapsulation does not interfere with the IR detection. The minimum thickness of the over-moulding is 1 mm to ensure biocompatibility strength over time. The resins manufactured by Epoxy Technology under the references EPO-TEK 301/301-2/301-2FL/302-3M may for example be used for the encapsulation of the electronic components.

The monitoring system 40 is fully encapsulated, preferably with a single-piece over-moulding, which ensures a very good sealing and insulation of the electrical components from the exterior. It further enables a much simpler manufacturing moulding process. Such moulding may for instance be a gravity moulding, with one or two pattern cavities made in Teflon.

Before encapsulation of the monitoring system 40, it is necessary to activate the power supply of such system as it will not be possible thereafter. Periodical detection will however not be performed as soon as it has not been first launched via the communication device 50, such that the monitoring system 40 remains in a sleep state, with a low power consumption. It is however preferable that the encapsulation of the monitoring system 40 is carried out immediately after having manufactured the mandibular repositioning device, so that the monitoring system 40 does not remain in a sleep state for a too long time.

Preferably, the encapsulated monitoring system 40 is arranged in a cavity provided in the mandibular repositioning device. This arrangement is such that the reflective IR detector will be facing the teeth when the mandibular repositioning device is positioned on the teeth of the patient.

Figure 8:
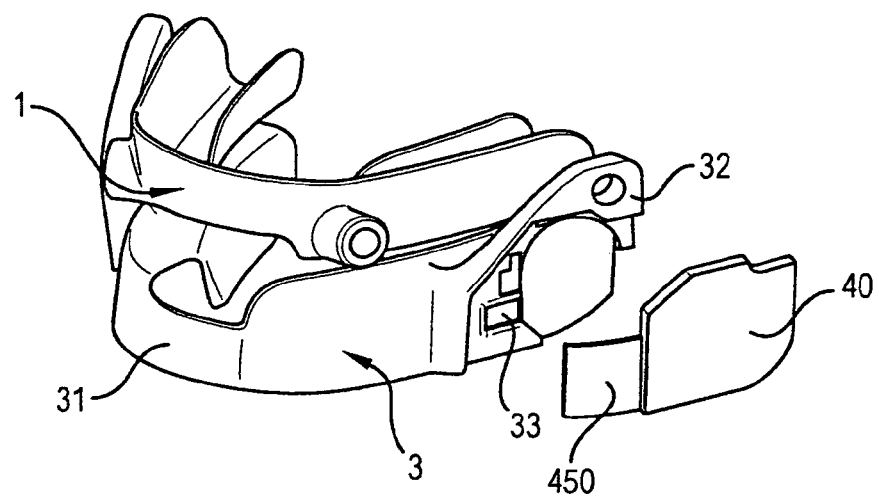
FIGS. 8 and 9 are perspective representations of a mandibular repositioning orthosis comprising a removable encapsulated monitoring system.
Figure 9:
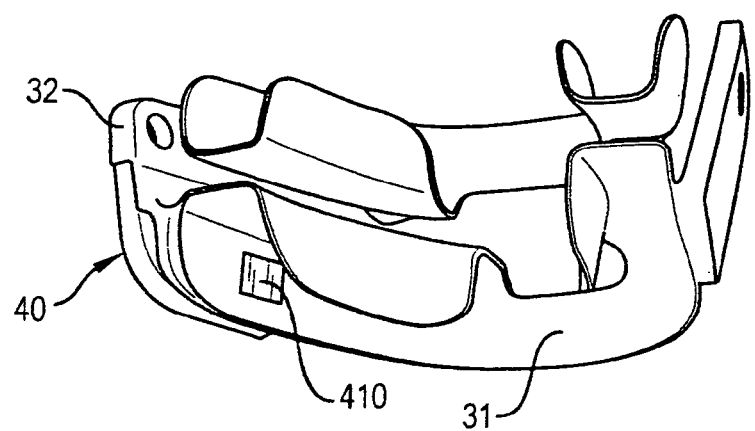

FIGS. 8 and 9 illustrate an embodiment of a mandibular repositioning device as described previously, provided with a bracket 32 extending from the lower portion 31 of the lower splint 3 (the tie rods are not represented). Such mandibular repositioning device is particularly adapted for integrating the encapsulated monitoring system 40 as a cavity may be formed within the bracket 32 and lower portion 31 of the lower splint 3 to receive the volume corresponding to the encapsulated monitoring system 40. An opening 33 is further provided through the wall of the lower splint 3 at a position where the reflective IR detector 410 of the monitoring system is to be located, such that the wall of the mandibular repositioning device does not interfere with the IR detection.

The encapsulated monitoring system 40 may for instance be clipped within the cavity provided in the mandibular repositioning device. Therefore, the encapsulated monitoring system 40 may be removed, for instance to be replaced by another encapsulated monitoring system when the battery has run down or in case of failure. Having a removable monitoring system 40 is particularly advantageous as the service life time of the mandibular repositioning device is much longer than the service life time of the monitoring system (about 6 years for the mandibular repositioning device compared to about 3 years for the proposed monitoring system).

Mandibular repositioning device do not have standard shape and are thus formed for a specific therapeutic treatment adapted to fit the shape of the mouth of the patient (in particular the shape and positioning of the teeth).

The mandibular repositioning device may thus be formed with a CADCAM technology (computer-aided design and computer-aided manufacturing) that enables designing and manufacturing the mandibular repositioning device taking into account several specifications, in particular with regard to the shape of the jaw of the patient (teeth specification) and with regard to the specific repositioning of the mandibula that is required to perform for preventing the patient to have sleep disorders (repositioning specification).

The encapsulated monitoring system 40 that is used for determining the compliant use of the orthosis by the patient has a specific definite shape that constitute a third specification (encapsulation specification) to take into account for designing and manufacturing the orthosis with CADCAM technology.

Consequently, the mandibular repositioning orthosis is preferably designed and manufactured with a CADCAM technology wherein the shape of the orthosis takes into account the three following specifications:
teeth specification;
repositioning specification; and
encapsulation specification.

The shape of the intraoral appliance, particularly the opposing surfaces of the first and second splint of the intraoral appliance, is/are preferably designed so that the opposing surfaces of the first and second splint are at least partially, preferably completely, abutting against each other in an advanced position or the lower jaw. The intraoral appliance may thus compensate the effects of the Christensen's phenomenon. The opening space between the back teeth is thus preferably reduced or compensated. Such an intraoral appliance provides a better wearing comfort.

The manufacturing process may comprise a step of selective laser sintering. Preferably the step is carried out in an automated fashion. The selective laser sintering may comprise the layer-wise sintering of a powder material. Any suitable material for producing a intraoral appliance may be used, which is suitable for laser sintering, which is biocompatible, and which is sufficiently rigid for the constraints. Preferably, a polymer material is used, most preferably polyamide is used. It is thus possible to efficiently and effectively produce an intraoral appliance that is preferably light and also comfortable to wear. The patients therefore do actually use the appliance more frequently leading to better treatment results. Moreover, the manufacturing time, labour costs as well as the material costs may be substantially reduced.

The specifications, such as the first three dimensional data set, or in other words, the teeth specification, may be obtained by scanning a dental impression provided by a dentist. Alternatively, the dentist or a third party may scan the particular shape and positioning of the teeth and jaws of a patient directly. The scan may then be send to the manufacturer of the intraoral appliance by known electronic communication means such as any kind of electronic file transfer. Thus the transportation time and costs may be reduced. Moreover, the risk of faulty or damaged dental impressions is eliminated or reduced. In overall, the quality of the intraoral appliance may be increased and the costs and manufacturing time may be decreased.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality.

The invention also covers all further features shown in the figures individually although they may not have been described in the afore description. The present invention covers further embodiments with any combination of features from different embodiments described above. Reference signs in the claims are provided merely as a clarifying example and shall not be construed as limiting the scope of the claims in any way. The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "essentially radial" shall also cover exactly radial).

The invention claimed is:

1. A compliance monitoring system for an intraoral appliance comprising:
a power source;
a detector including at least one signal emitter and at least one signal receiver, and configured to detect signals received by the signal receiver when the intraoral appliance is positioned in the mouth for use; and
a transponder configured to communicate measured data, corresponding to the signals received by the signal receiver, to a remote processing system,
wherein the monitoring system is configured to, based on signals received by the signal receiver and representing a particular property of a patient or a group of patients, adjust wave length, intensity, amplitude, frequency, phase, modulation, coding or impedance of the detector signal emitter or signal receiver, and the signal emitter and the signal receiver are separately adjustable.

2. The compliance monitoring system of claim 1, wherein the signal emitter or the signal receiver is adjustable based on a unique characteristic of a patient or a group of patients.

3. The compliance monitoring system of claim 1, wherein the particular property is a physical property including one or more of the group consisting of colour, teeth enamel, temperature, distance, angle, shape, and wherein the colour is colour of gum, teeth, or inside of cheek.

4. The compliance monitoring system of claim 1, wherein the remote processing system is configured to determine and report compliant or non-compliant use of the intraoral appliance based on measured data received from the transponder.

5. The compliance monitoring system of claim 1, wherein the signal emitter is an infrared-light emitter, and wherein the signal receiver is an infrared-light receiver.

6. The compliance monitoring system of claim 1, wherein the signal emitter is an ultra sound emitter, and wherein the signal receiver is an ultra sound receiver.

7. The compliance monitoring system of claim 1, wherein the signal emitter is a current emitter, and wherein the signal receiver is a voltage receiver.

8. The compliance monitoring system in accordance with claim 1, wherein the at least one signal emitter and the at least one signal receiver are adjustable and/or are adapted for being calibrated.

9. The compliance monitoring system of claim 1, wherein the at least one signal emitter and/or the at least one signal receiver of the monitoring system is automatically adjustable.

10. The compliance monitoring system of claim 1, the signal emitter or the signal receiver is adjusted based on signal measurements by the signal receiver while the signal emitter is controlled to emit a signal, and signal measurements by the signal receiver while the signal emitter is controlled to not emit a signal.

11. The compliance monitoring system in accordance with claim 1, wherein the signal emitter and the signal receiver are configured to be operated with a wavelength adapted for:
   reflection on the specific enamel of a patient's tooth or teeth;
   the individual relative position between emitter, receiver and tooth; and/or
   distance, angle, shape/geometry, colour, surface properties, type of tooth, temperature, and/or fluid media in contact with the emitted and/or reflected signal.

12. The compliance monitoring system in accordance with claim 1, wherein the detector is a reflective detector.

13. The compliance monitoring system of claim 1, wherein the transponder is a radiofrequency identification transponder having a radiofrequency identification modulator/demodulator and a data storage medium.

14. The compliance monitoring system of claim 1, further comprising a recorder configured to record measurement data and a controller configured for periodical activation of the detector including a reflective infra-red detector and the recorder.

15. The compliance monitoring system of claim 14, wherein the controller comprises a crystal, an oscillator, a prescaler and a timer.

16. The compliance monitoring system of claim 1, further comprising a processor to process the measured data and associated time data, wherein the compliance monitoring system is further configured to record said processed measurement data and associated processed time data.

17. The compliance monitoring system of claim 16, wherein the processed measurement data and associated processed time data correspond to the accumulated period of time the intraoral appliance has been used in a specific day.

18. The compliance monitoring system of claim 16, wherein the processor is programmable to either store raw measurement data and associated time data, or to store processed measurement data and associated time data.

19. An intraoral appliance, comprising at least one splint, wherein said at least one splint is further designed for receiving the compliance monitoring system of claim 1 in a position where the detector faces at least one of the teeth.

20. A mandibular repositioning device comprising a compliance monitoring system according to claim 1, and at least one splint configured to receive the compliance monitoring system in a position where the detector faces at least one of the teeth.

21. An apparatus determining compliant use of an intraoral appliance, comprising:
   the compliance monitoring system of claim 1, and
   a processing system comprising a communication device and an analysing device wherein
   the communication device is configured for retrieving data from and for sending command data to the compliance monitoring system, and
   the analysing device is communicatively coupled to the communication device and is configured for identifying, collecting and organising information from the monitoring system via the communication device in order to determine and report compliant or non-compliant use of the intraoral appliance.

22. A method for determining compliant use of an intraoral appliance with a compliance monitoring system in accordance to claim 1, comprising the steps of:
   measuring a value $V_{CE}$ indicative of a signal received by the signal receiver; and
   determining whether a tooth is detected or not by comparing the value $V_{CE}$ to a threshold value.

23. The method of claim 22, further comprising the steps of:
   measuring a first value $V_{CE1}$ while the signal emitter does not emit a signal
   measuring a second value $V_{CE2}$ while the signal emitter emits a signal; and
   calculating the difference delta $V_{CE}$ between the second value $V_{CE2}$ and the first value $V_{CE1}$.

24. The method of claim 23, wherein the value $V_{CE}$ to be compared with the threshold value is the difference delta $V_{CE}$.

25. The method of claim 22, wherein the signal received by the signal receiver is based on a signal emitted by the signal emitter, wherein the signal is influenced by a physical property or by a unique characteristic of the patient.

26. The method in accordance with claim 22, wherein the compliance monitoring system is adjusted and/or calibrated by conducting at least one measurement outside the patient's oral cavity and a plurality of measurements inside the patient's oral cavity including changing the settings of the signal emitter and/or the signal receiver.

27. The method in accordance with claim 26, wherein the signal emitter and/or signal receiver is/are adjusted by changing the hardware settings of the compliance monitoring system, signal emitter and/or signal receiver.

28. The method in accordance with claim 22, wherein the threshold value and/or the adjustments of the signal emitter and/or signal receiver are determined during calibration.

29. The method in accordance with claim 22, wherein calibration comprises measuring a plurality of differences delta $V_{CEx}$ obtained for different adjustments of the signal emitter and/or signal receiver in at least two different setups, one setup with the intraoral appliance in the application position and one setup with the intraoral appliance in a position outside the oral cavity.

30. The method in accordance with claim 22, including the step of automated laser sintering of the intraoral appliance for attaching the compliance monitoring system.

31. The method of claim 30, further comprising the steps of obtaining a first three dimensional data set of the lower jaw and teeth of a patient, of the upper jaw and teeth of a patient and/or of the occlusal plane of closed jaws of a patient;
obtaining a second three dimensional data set of a customized oral appliance, by means of computer aided design based on the first three dimensional data set; and automated manufacturing of a customized oral appliance.

32. A compliance monitoring system coupled to an intraoral appliance configured to be positioned in the mouth, the compliance monitoring system comprising:
a power source;
a detector coupled to the power source and including a signal emitter and a signal receiver;
a transponder configured to communicate measured data to a remote processing system; and
a processing system comprising at least one processor, wherein the processing system is coupled to the detector and is at least configured to:
control the signal emitter to periodically emit a signal inside of the mouth;
receive, from the signal receiver, measurements of signals inside of the mouth captured by the signal receiver based on the signal emitted by the signal emitter;
adjust one or more parameters including wave length, intensity, amplitude, frequency, phase, modulation, coding or impedance of the signal emitter or the signal receiver based on the received measurements of signals inside of the mouth from the signal receiver, wherein the signal emitter and the signal receiver are separately adjustable; and
communicate, using the transponder, the received measurements from the signal receiver.

33. The compliance monitoring system of claim 32, wherein the one or more parameters are adjusted based on a plurality of measurements of the signals captured by the signal receiver.

34. The compliance monitoring system of claim 33, wherein the one or more parameters are adjusted based on (1) at least one measurement of the signals captured by the signal receiver while the signal emitter is controlled to not emit a signal and (2) at least one measurement of the signals captured by the signal receiver while the signal emitter is controlled to emit a signal.

35. A compliance monitoring system coupled to an intraoral appliance configured to be positioned in the mouth, the compliance monitoring system comprising:
a power source;
a detector coupled to the power source and including a signal emitter and a signal receiver;
a transponder configured to communicate measured data to a remote processing system; and
a processing system comprising at least one processor, wherein the processing system is coupled to the detector and is at least configured to:
control the signal emitter to periodically emit a signal inside of the mouth;
receive, from the signal receiver, measurements of signals inside of the mouth captured by the signal receiver based on the signal emitted by the signal emitter;
adjust one or more parameters including wave length, intensity, amplitude, frequency, phase, modulation, coding and/or impedance of at least one of the signal emitter and the signal receiver based on the received measurements of signals inside of the mouth from the signal receiver, wherein the one or more parameters are adjusted based on signal measurements by the signal receiver while the signal emitter is controlled to emit a signal, and signal measurements by the signal receiver while the signal emitter is controlled to not emit a signal; and
communicate, using the transponder, the received measurements from the signal receiver.

36. A compliance monitoring system coupled to an intraoral appliance configured to be positioned in the mouth, the compliance monitoring system comprising:
a power source;
a detector coupled to the power source and including a signal emitter and a signal receiver;
a transponder configured to communicate measured data to a remote processing system; and
a processing system comprising at least one processor, wherein the processing system is coupled to the detector and is at least configured to:
control the signal emitter to periodically emit a signal inside of the mouth;
receive, from the signal receiver, measurements of signals inside of the mouth captured by the signal receiver based on the signal emitted by the signal emitter;
adjust one or more parameters including wave length, intensity, amplitude, frequency, phase, modulation, coding and/or impedance of at least one of the signal emitter and the signal receiver based on the received measurements of signals inside of the mouth from the signal receiver, wherein adjusting one or more parameters includes changing a wiring configuration of the at least one of the signal emitter and the signal receiver; and
communicate, using the transponder, the received measurements from the signal receiver.

37. The compliance monitoring system of claim 1, wherein a wavelength of the signal emitter is adjusted based on at least one signal measurement by the signal receiver while the intraoral appliance is positioned in the mouth for use, and a plurality of signal measurements by the signal receiver while the intraoral appliance is positioned outside of the mouth.

* * * * *